(12) United States Patent
Brannan et al.

(10) Patent No.: US 12,064,177 B2
(45) Date of Patent: *Aug. 20, 2024

(54) MODULAR MICROWAVE GENERATORS AND METHODS FOR OPERATING MODULAR MICROWAVE GENERATORS

(71) Applicant: Covidien LP, Mansfield, MA (US)

(72) Inventors: Joseph D. Brannan, Lyons, CO (US); Robert J. Behnke, II, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,941

(22) Filed: Feb. 17, 2023

(65) Prior Publication Data

US 2023/0190372 A1   Jun. 22, 2023

Related U.S. Application Data

(63) Continuation of application No. 15/598,391, filed on May 18, 2017, now Pat. No. 11,583,336.

(Continued)

(51) Int. Cl.
*A61B 18/18* (2006.01)
*H05B 6/64* (2006.01)
(Continued)

(52) U.S. Cl.
CPC ....... *A61B 18/1815* (2013.01); *H05B 6/6447* (2013.01); *H05B 6/645* (2013.01);
(Continued)

(58) Field of Classification Search
CPC ...... A61B 18/1815; A61B 2017/00973; A61B 2018/00577; A61B 2018/00648;
(Continued)

(56) References Cited

U.S. PATENT DOCUMENTS 6,186,959 B1   2/2001   Canfield et al.
8,225,015 B2   7/2012   Gao-Saari et al.
(Continued)

OTHER PUBLICATIONS

Extended European Search Report for application No. 17172011.3 dated Oct. 13, 2017 (9 pages).

(Continued)

*Primary Examiner* — Eun Hwa Kim
*Assistant Examiner* — Catherine C. Premraj
(74) *Attorney, Agent, or Firm* — Carter, DeLuca & Farrell LLP

(57) ABSTRACT

The modular microwave ablation system of the present disclosure includes a microwave instrument, a microwave generator, and one or more auxiliary modules that include circuitry for performing functions related to the operation of the microwave generator. The one or more auxiliary modules are removably connected to the microwave generator. The microwave generator includes a microwave signal generator that generates a microwave signal; a microwave generator controller in communication with the microwave signal generator; one or more terminals that connect to the one or more auxiliary modules, respectively; and a power supply and/or a power distribution module coupled to the microwave signal generator, the microwave generator controller, and the one or more terminals. The one or more terminals provide (1) power from the power supply and/or power distribution module to the one or more respective auxiliary modules and (2) communication signals to and from the one or more respective auxiliary modules.

20 Claims, 20 Drawing Sheets

Related U.S. Application Data

(60) Provisional application No. 62/338,599, filed on May 19, 2016.

(51) Int. Cl.
  *H05B 6/70* (2006.01)
  *A61B 17/00* (2006.01)
  *A61B 18/00* (2006.01)

(52) U.S. Cl.
  CPC ...... *H05B 6/70* (2013.01); *A61B 2017/00973* (2013.01); *A61B 2018/00577* (2013.01); *A61B 2018/00648* (2013.01); *A61B 2018/00702* (2013.01); *A61B 2018/00785* (2013.01); *A61B 2018/00791* (2013.01); *A61B 2018/00827* (2013.01); *A61B 2018/00892* (2013.01); *A61B 2018/00988* (2013.01); *A61B 2018/1823* (2013.01)

(58) Field of Classification Search
  CPC ........... A61B 2018/00702; A61B 2018/00785; A61B 2018/00791; A61B 2018/00827; A61B 2018/00892; A61B 2018/00988; A61B 2018/1823; H05B 6/6447; H05B 6/645; H05B 6/70
  See application file for complete search history.

(56) References Cited

U.S. PATENT DOCUMENTS

| | | |
|---|---|---|
| 8,242,782 B2 | 8/2012 | Brannan et al. |
| 8,568,401 B2 | 10/2013 | Brannan |
| 8,615,374 B1 | 12/2013 | Discenzo |
| 8,852,179 B2 | 10/2014 | Ward et al. |
| 11,583,336 B2 | 2/2023 | Brannan et al. |
| 2005/0222566 A1 | 10/2005 | Nakahira |
| 2005/0283148 A1 | 12/2005 | Janssen et al. |
| 2006/0224152 A1 | 10/2006 | Behnke et al. |
| 2012/0078139 A1 | 3/2012 | Aldridge et al. |
| 2013/0345693 A1* | 12/2013 | Brannan ............ A61B 18/1815 439/502 |
| 2014/0022245 A1 | 1/2014 | Brannan et al. |
| 2014/0246478 A1 | 9/2014 | Baber et al. |
| 2015/0112320 A1 | 4/2015 | Brannan |
| 2015/0282857 A1 | 10/2015 | Anderson et al. |
| 2015/0282860 A1 | 10/2015 | Anderson et al. |
| 2015/0282861 A1 | 10/2015 | Anderson et al. |
| 2015/0320478 A1 | 11/2015 | Cosman, Jr. |
| 2016/0008069 A1 | 1/2016 | Brannan |
| 2020/0078609 A1 | 3/2020 | Messerly |

OTHER PUBLICATIONS

Test & Measurement R&S CMW500 Wideband Radio Communiation Tester Specifications Advanced Test Equipment Rentals Contents, May 31, 2013 (72 pages).
Japanese Office Action for application No. 2017-099700 dated Jan. 25, 2018.
Australian Examination Report for application No. 2017203359 dated Jul. 30, 2018, 3 pages.
Canadian Office Action for application No. 2,967,728 dated Mar. 5, 2018, 4 pages.
Australian Examination Report No. 3 issued in corresponding Appl. No.: AU 2017203359, dated Dec. 4, 2018 (4 pages).
Japanese Office Action issued in corresponding Appl. No. JP 2017-099700, mailed Aug. 27, 2018, together with English language translation (22 pages).
Extended European Search Report issued in corresponding application EP 21154588.4 dated May 19, 2021 (6 pages).
Australian Examination Report No. 1 issued in corresponding Appl. No. AU 2019201379 dated Feb. 13, 2020 (3 pages).

* cited by examiner

MODULAR MICROWAVE GENERATORS AND METHODS FOR OPERATING MODULAR MICROWAVE GENERATORS

CROSS-REFERENCE TO RELATED APPLICATIONS

This application is a continuation of U.S. patent application Ser. No. 15/598,391, filed on May 18, 2017, now U.S. Pat. No. 11,583,336, which claims the benefit of the filing date of provisional U.S. Patent Application No. 62/338,599, filed on May 19, 2016.

FIELD

The present disclosure relates to modular microwave generators and to methods for operating modular microwave generators including modules with localized and compartmentalized processors, memory, and/or other structures for performing auxiliary functions relating to microwave ablation procedures.

BACKGROUND

In microwave ablation, electromagnetic fields are used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes to heat or ablate the tissue.

Typically, systems for microwave ablation procedures include a microwave generator and a microwave instrument such as an ablation probe having an antenna assembly. The microwave generator and microwave instrument are operatively coupled to each other by a coaxial cable for carrying microwave signals from the microwave generator to the microwave instrument. Microwave generators typically include circuitry for generating microwave signals and a controller for controlling the operation of the circuitry and controlling a user interface, such as a display, including user controls for setting characteristics of the microwave signals, such as buttons for adjusting the power level of the microwave signals.

Some microwave generators may incorporate additional features, such as a temperature measurement device or a microwave signal measurement device, to the assist the user in performing an ablation procedure. However, the user may not be able to update or reconfigure those additional features to keep up with the latest technologies or to meet the changing needs of a user. In some cases, the user may not even need some or all of the additional features. In other cases, the microwave generator may not include or be compatible with new or updated features needed by the user.

SUMMARY

In an aspect, the present disclosure features a microwave generator for generating microwave signals. The microwave generator includes a microwave signal generator configured to generate a microwave signal, a microwave generator controller in communication with the microwave signal generator, a power supply electrically coupled to the microwave signal generator and the microwave generator controller, and one or more terminals configured to connect to one or more respective auxiliary modules, each of which includes an electrical isolation circuit, a hardware processor, and a memory coupled to each other.

The one or more terminals provide (1) power from the power supply to the one or more respective auxiliary modules via the microwave generator controller and (2) communication signals to and receiving communication signals from the one or more respective auxiliary modules to enable the one or more auxiliary modules to perform at least one operation independent of the microwave signal generator and the power supply.

In another aspect, the microwave generator includes a power distribution module electrically connected between (1) the power supply and (2) the microwave signal generator, the microwave generator controller, and the one or more terminals. The power distribution module conditions the power output from the power supply and provides the conditioned power to the microwave signal generator, the microwave generator controller, and the one or more auxiliary modules.

In another aspect, the microwave generator includes a communications bus coupled between the microwave generator controller and the one or more terminals. The microwave generator controller acquires data from the one or more terminals via the communications bus and stores the data in memory of the microwave generator controller.

In another aspect, the communications bus is coupled between the microwave generator controller and the microwave signal generator and the microwave generator controller transmits a portion of the data stored in the memory to the microwave signal generator.

In aspects, the power distribution module, the microwave signal generator, the microwave generator controller, and the one or more auxiliary modules include respective field programmable gate arrays (FPGAs) coupled to the communications bus.

In aspects, the microwave generator controller controls the microwave signal generator to generate a desired microwave signal.

In another aspect, the one or more auxiliary modules include an instrument monitoring module configured to receive information relating to a state or identity of the instrument.

In yet another aspect, the one or more auxiliary modules include a temperature monitoring module configured to monitor the temperature of a temperature probe.

In a further aspect, the one or more auxiliary modules include a user interface module configured to receive user inputs.

In another aspect, the microwave generator further includes a communications bus, wherein the one or more terminals are configured to communicate with the microwave generator controller via the communications bus.

In yet another aspect, each of the signal generator, the power supply, and the one or more auxiliary modules includes a power isolation circuit.

In a further aspect, the present disclosure features a microwave ablation system including a microwave generator, a microwave instrument coupled to the microwave generator, and one or more auxiliary modules removably coupled to the microwave generator and including respective auxiliary controllers that independently control the circuitry of the one or more auxiliary modules and respective power isolation circuits that electrically isolate the one or more auxiliary modules from the microwave generator. The microwave generator includes a microwave signal generator configured to generate a microwave signal, a microwave generator controller in communication with the microwave signal generator, a power supply electrically coupled to the microwave signal generator and the microwave generator controller, and one or more terminals configured to receive the one or more respective auxiliary modules. The power supply is configured to receive input power and independently supply output power to the microwave signal generator and the microwave generator controller, and the one or more terminals provide: (1) power from the power supply to the one or more respective auxiliary modules via the microwave generator controller and (2) communication signals to the one or more respective auxiliary modules to enable the one or more auxiliary modules to operate independently of the microwave signal generator and the power supply.

In another aspect, the microwave generator includes a power distribution module electrically connected between (1) the power supply and (2) the microwave signal generator, the microwave generator controller, and the one or more terminals. The power distribution module conditions the power output from the power supply and provides the conditioned power to the microwave signal generator, the microwave generator controller, and the one or more auxiliary modules.

In another aspect, the microwave generator includes a communications bus coupled between the microwave generator controller and the one or more terminals. The microwave generator controller acquires data from the one or more terminals via the communications bus and stores the data in memory of the microwave generator controller.

In another aspect, the communications bus is coupled between the microwave generator controller and the microwave signal generator and the microwave generator controller transmits a portion of the data stored in the memory to the microwave signal generator.

In aspects, the power distribution module, the microwave signal generator, the microwave generator controller, and the one or more auxiliary modules include respective field programmable gate arrays (FPGAs) coupled to the communications bus.

In aspects, the microwave generator controller controls the microwave signal generator to generate a desired microwave signal.

In another aspect, the microwave instrument is a microwave ablation probe.

In another aspect, the microwave instrument includes a memory having stored thereon information that is retrieved by the microwave generator or transmitted by the microwave instrument to the microwave generator.

In another aspect, the stored information is instrument identification information.

In another aspect, the instrument is an ablation tool including information communicable to the generator.

In another aspect, the system further comprises a temperature probe.

In another aspect, the one or more auxiliary modules include a remote temperature monitoring module configured to monitor a temperature of the temperature probe.

In another aspect, the one or more auxiliary modules include instrument monitoring module configured to receive information of a state and identity of an instrument.

In another aspect, the one or more auxiliary modules include a user interface module configured to receive user inputs.

In a further aspect, the present disclosure features a method of controlling a modular microwave generator including supplying power to a power distribution module, converting the supplied power to regulated power, supplying the regulated power to the microwave signal generator and one or more auxiliary modules while the one or more respective auxiliary modules are coupled to the microwave generator controller, converting the regulated power to isolated power at the microwave power generator and at each of the one or more auxiliary modules, transmitting, by the microwave generator controller, communication signals to the one or more respective auxiliary modules while the one or more respective auxiliary modules are coupled to the microwave generator controller to configure at least one setting of each of the one or more auxiliary modules, performing localized processing at the microwave generator controller and the one or more auxiliary modules, and controlling, by the microwave generator controller, the microwave signal generator to generate a desired microwave signal based on the communication signals received from at least one of the one or more auxiliary modules.

In another aspect, the method includes receiving, at an instrument monitoring module coupled to the generator controller, information of a state and identity of a microwave instrument with an instrument monitoring module, transmitting, by an instrument monitoring module, the received information of a state and identity of the microwave instrument to the microwave generator controller, and processing the state and identity information to determine the desired microwave signal.

In another aspect, the method includes displaying the state and identity information on a display.

In another aspect, the method further includes monitoring, by a temperature monitoring module, temperature of a temperature probe with a temperature monitoring module, transmitting, by the temperature monitoring module, the received temperature of the temperature probe to the microwave generator controller, and processing the received temperature to determine the desired microwave signal or display the received temperature on a display.

In another aspect, the method includes receiving, at a user interface module, a user input, transmitting, by the user interface module, the user input to the microwave generator controller, and processing the user input to determine the desired microwave signal, a power limitation, a temperature limitation, or a display option.

In another aspect, providing communication signals includes sending and receiving signals via a communication bus.

In another aspect, the method includes applying the desired microwave signal to target tissue to ablate the target tissue.

In another aspect, the method further includes receiving updated code for the one or more auxiliary modules, determining, by the microwave generator controller, whether the one or more auxiliary modules are coupled to the microwave generator, determining whether the one or more auxiliary modules include updated code when it is determined that the one or more auxiliary modules are coupled to the microwave generator, and updating, by the microwave generator controller, the one or more auxiliary modules with the updated code when it is determined that the one or more auxiliary modules include updated code.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings. In the following description, well-known functions or constructions are not described in detail to avoid obscuring the present disclosure in unnecessary detail.

Microwave generators may perform several functions in addition to and relating to the main function of generating a microwave signal to be used by a microwave instrument. While additional features add utility to a microwave generator, they also require more power, use more processing resources, and add to the overall price. The present disclosure relates to a modular microwave generator system that includes physical modules with decentralized and isolated processing to perform auxiliary functions associated with the microwave generator. The modules may be added to and removed from the microwave generator as necessary, allowing a user to purchase and enable only those functions needed for a given procedure.

Figure 1:
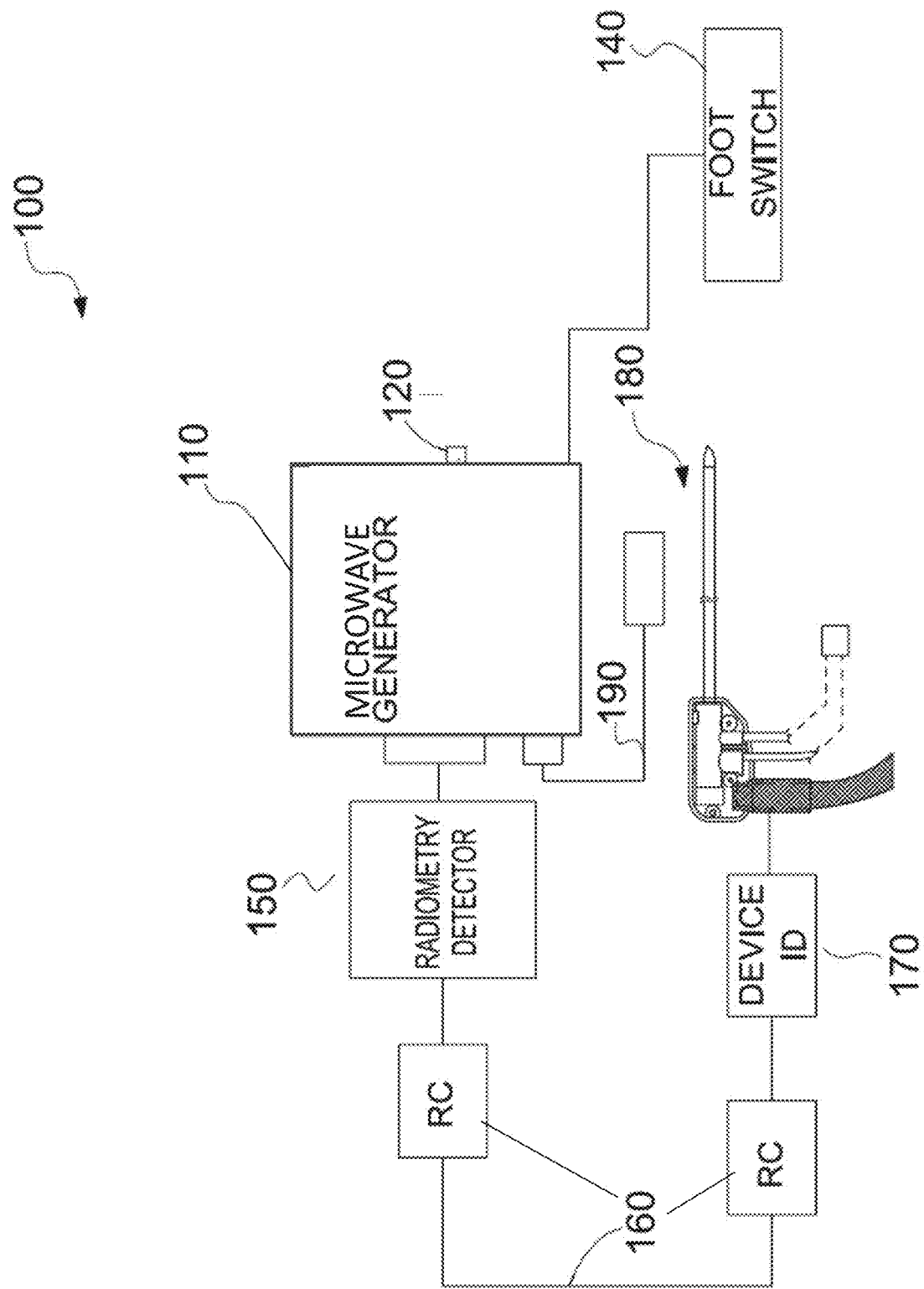
FIG. 1 is a block diagram of a microwave ablation system according to embodiments of the present disclosure.

FIG. 1 is a block diagram of a microwave ablation system in accordance with embodiments of the present disclosure. As shown in FIG. 1, the microwave ablation system 100 includes a microwave generator 110 and a microwave applicator or a microwave instrument 180. The microwave generator 110 and microwave instrument 180 are connected together by a reusable cable 160. The microwave instrument 180 may be associated with device ID memory 170 storing an identifier or a device ID. The device ID memory 170 may be incorporated within the microwave instrument 180 or may be a memory formed, for example, in a separate connector or adapter configured to mate with a connector of the reusable cable 160. Thus, the reusable cable 160 connects to the device ID memory 170, which, in turn, connects to the microwave instrument 180. Similar memories storing device ID information may be included in the reusable cable 160 and the radiometer 150. The microwave generator 110 may also be connected to a footswitch 140, which may include a memory storing a device ID, via a footswitch port on the microwave generator 110.

During the use of the microwave ablation system 100, a variety of different subsystems may be required. Typically, the operation of the subsystems is controlled by a microprocessor-driven console (e.g., the microwave generator 110). The microprocessor receives mechanical inputs from either the user or operator of the microwave ablation system 100 or from an assistant. A control input device, such as the footswitch 140, is used to accept mechanical inputs from the operator so that the operator can govern the operation of the subsystems within the microwave ablation system 100. When actuated by an operator, the control input device transmits electrical signals to the microprocessor control system. The electrical signals are then used to control the operational characteristics of a subsystem in the microwave ablation system 100.

Microwave generator 110, as shown in FIG. 1, also includes digital port 120. Digital port 120 is configured to receive a connector to establish connections with a programming device or a device intended to communicate with individual components or modules of the microwave generator 110 (see FIG. 2). The programming device, while connected to digital port 120, may communicate and program the individual modules through generator controller 220.

As shown in FIG. 1, the microwave generator 110 is connected to a remote temperature probe 190. The remote temperature probe 190 may include a temperature sensor such as a thermocouple or a thermistor, and may include a memory storing a device ID or other information such as status information. The remote temperature probe 190 is operable to measure temperature of tissue at a surgical site. In one embodiment, the remote temperature probe 190 is configured to continuously output the temperature signal to the microwave generator 110 allowing a user to observe the temperature or to control the microwave generator 110.

Figure 2:
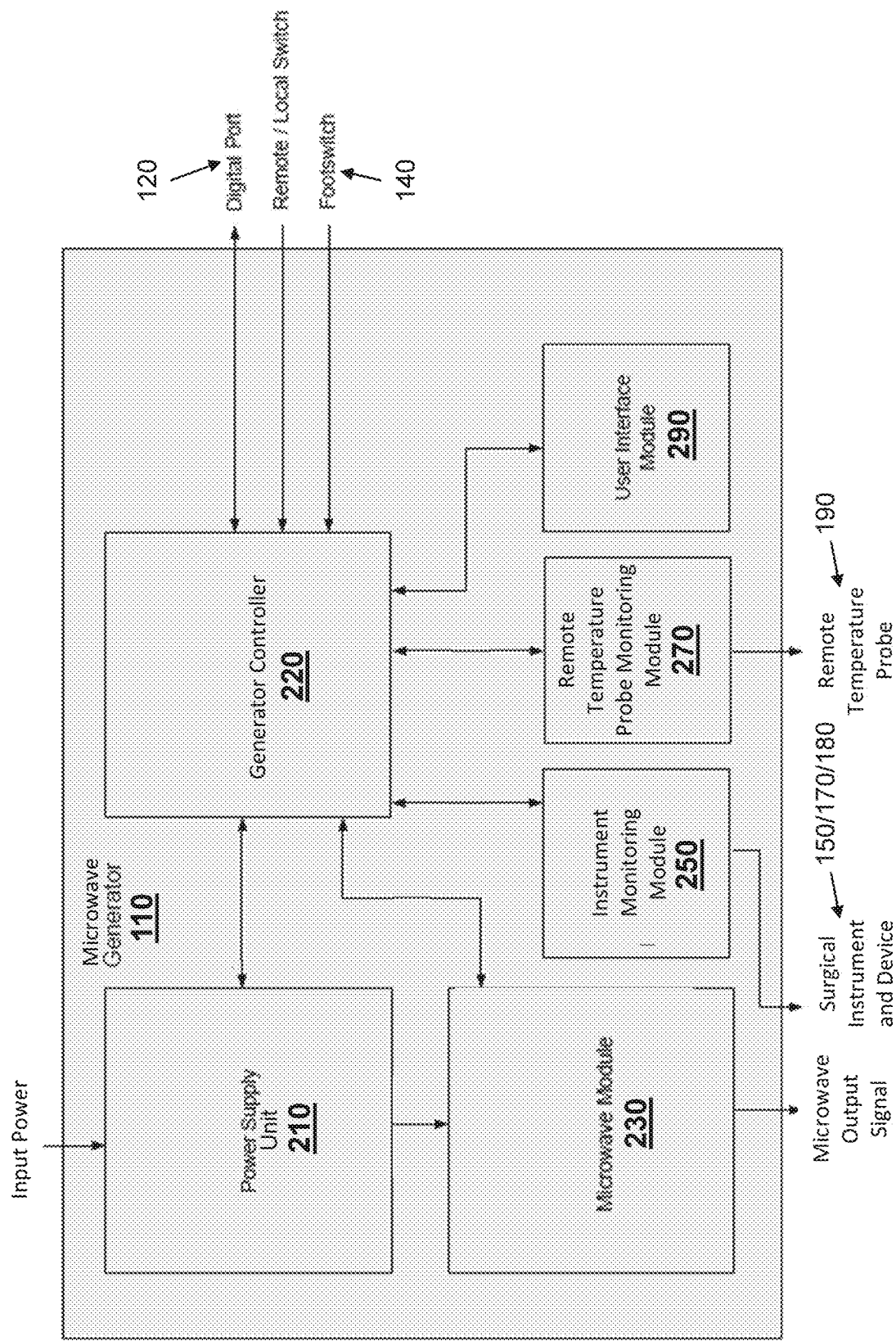
FIG. 2 is a circuit block diagram of the microwave generator of FIG. 1 according to an embodiment of the present disclosure.

FIG. 2 is a circuit block diagram of the microwave generator 110 of FIG. 1, which is configured to output microwave signals according to an embodiment of the present disclosure. Microwave generator 110 may include any of, a subset of, or all of a power supply module or unit 210, a generator control module or generator controller 220, a microwave module 230, an antenna or instrument monitoring module 250, a remote temperature probe monitoring board or module 270, and a user interface module 290.

The power supply unit 210 is electrically connected to the generator controller 220 and the microwave module 230 to supply power to the generator controller 220 and the microwave module 230. The generator controller 220, in turn, is electrically connected to the antenna or instrument monitoring module 250, the remote temperature probe monitoring board or module 270, and the user interface module 290 by electrical conductors, such as wires or traces, for supply power to the antenna or instrument monitoring module 250, the remote temperature probe monitoring board or module 270, and the user interface module 290. The generator controller 220 is also in communication with the instrument monitoring module 250, the remote temperature probe monitoring board or module 270, and the user interface module 290 through a communications conduit such as the electrical conductors described above, optical fibers, or a wireless communications link.

In embodiments, any of, a subset of, or all of these modules may be removably connectable to ports or terminals of the microwave generator 110. For example, only the auxiliary modules, e.g., the instrument monitoring module 250, the remote temperature probe monitoring module 270, and the user interface module 290, may be removably connected to the microwave generator 110 and the other modules may be more permanently built into the microwave generator 110.

Figure 3:
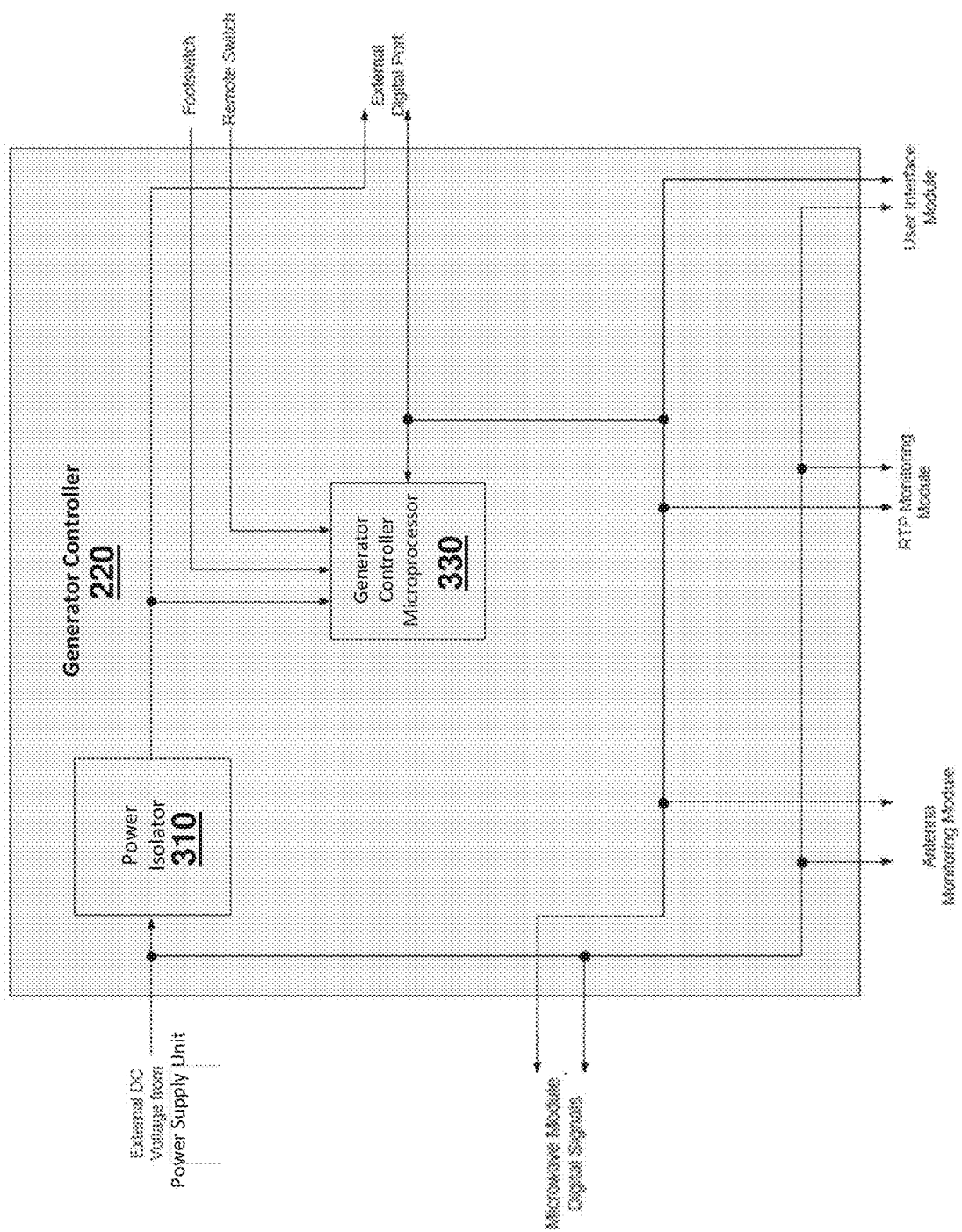
FIG. 3 is a circuit block diagram of a generator controller of the microwave generator of FIG. 2 according to an embodiment of the present disclosure.

FIG. 3 illustrates generator controller 220 of microwave generator 110 according to an embodiment of the present disclosure. Generator controller 220 includes a power isolator 310 that receives external DC voltage from power supply unit 210. The power isolator 310 may include a transformer having a primary winding and a secondary winding. Power received by power isolator 310 passes through the primary winding of the transformer, which induces a current in the secondary winding of the transformer proportional to the current received by power isolator 310. The induced current provides power to generator controller microprocessor 330. In an embodiment, power isolator 310 supplies power to generator controller microprocessor 330 at, for example, 12 VDC with a maximum power draw of 50 W. Generator controller microprocessor 330 further supplies 12 VDC to the generator subsystems, including microwave module 230, instrument monitoring module 250, remote temperature probe monitoring module 270, and user interface module 290.

Power isolator 310 further provides isolated power to a device connected to an external digital port of microwave generator 110. An optocoupler may be substituted in place of a transformer in power isolator 310. Power isolator 310 may also include voltage level shifters and buck and/or boost converters.

Generator controller microprocessor 330 is a programmable processor configured through flash programming, or through other suitable programming methods and languages, to communicate digitally with microwave module 230, instrument monitoring module 250, remote temperature probe monitoring module 270, user interface module 290, footswitch 140, other remote switches, and a device connected to digital port 120 of microwave generator 110. Generator controller microprocessor 330 may be calibrated through software calibration methods including radix-based digital self-calibration, background equivalent radix extraction, interference cancelling, or hardware calibration methods including the use of, for example, comparator/digital-to-analog converter (DAC) combinations, digitally controllable low-pass filters using a digital potentiometer, calibration-multiplexers, or any hardware and/or software solutions, to improve the digital communications links. As part of its communication with microwave module 230, instrument monitoring module 250, remote temperature probe monitoring module 270, and user interface module 290, generator controller microprocessor 330 communicates information regarding the generator controller microprocessor 330 including, for example, status information, serial number, and firmware version to each component, while receiving, from each component, information regarding the generator controller microprocessor 330 including, for example, status information, serial number, and firmware version, which generator controller microprocessor 330 continually processes and monitors.

Generator controller microprocessor 330 digitally communicates with user interface module 290 to receive user inputs and send information that may be communicated to a user by user interface module 290. Generator controller microprocessor 330 may issue a signal to user interface module 290 causing user interface module 290 to prompt a user to enter a microwave power level or a treatment time. Upon user selection, user interface module 290 sends generator controller microprocessor 330 a signal indicating the selection and generator controller microprocessor 330 receives and processes the signal before issuing signal to microwave module 230 to set the power level or treatment time. In the alternative, generator controller microprocessor 330 may delay a signal to microwave module 230. For instance, if generator controller microprocessor 330 receives a treatment time, generator controller microprocessor 330 sends a signal to microwave module 230 only when the allotted time has ended. While the treatment occurs, generator controller microprocessor 330 counts down the selected treatment time. In addition to issuing an end signal to microwave module 230, generator controller microprocessor 330 communicates with user interface module 290 throughout the countdown to send user interface module 290 information regarding the remaining treatment to display including the remaining treatment time to indicate to a user how much time remains.

Generator controller microprocessor 330 may additionally issue command signals to user interface module 290 causing user interface module 290 to prompt a user to reset a system startup default state. Upon receiving a user input, user interface module 290 sends a signal to user interface module 290 indicating the user input. If user interface module 290 receives a reset signal, settings saved in a memory of user interface module 290 are erased and replaced with factory default settings saved in long term memory.

Generator controller microprocessor 330 may additionally issue command signals to user interface module 290 causing user interface module 290 to prompt a user to set an interlock state. Example interlock state conditions include, but are not limited to, temperature, voltage, current, and/or power limits. Additional ranges and limits may be factory set or established according to an equation dependent on particular settings selected by the user. Generator controller microprocessor 330 receives temperature information from Remote temperature probe monitoring module 270 and power information from microwave module 230.

If a measurement deviates beyond an interstate lock or an additional range or limit, generator controller microprocessor 330 causes microwave module 230 to halt the application of microwave energy and issues a signal to user interface module 290 to cause user interface module 290 to display an indicator that the interstate lock or an additional range or limit has been exceeded. If an interstate lock has been exceeded, user interface module 290 may prompt the user to acknowledge, clear, and/or alter the interlock state.

Generator controller microprocessor 330 may additionally issue command signals to user interface module 290 causing user interface module 290 to display various pieces of information, including, but not limited to, tool temperature, tool identity, type and model of modules present, and/or errors. A user may select to acknowledge and/or clear a displayed piece of information, and generator controller microprocessor 330 will signal user interface module 290 to discontinue the display of the chosen information.

Generator controller microprocessor 330 may additionally issue a signal to user interface module 290 causing user interface module 290 to prompt a user to start and stop an ablation procedure. If a start or stop input is received from the user, generator controller microprocessor 330 signals microwave module 230 to begin or discontinue the application of a microwave signal. In the alternative, a user may cause generator controller microprocessor 330 to start or stop an ablation procedure by depressing or ceasing to depress footswitch 140.

Figure 4:
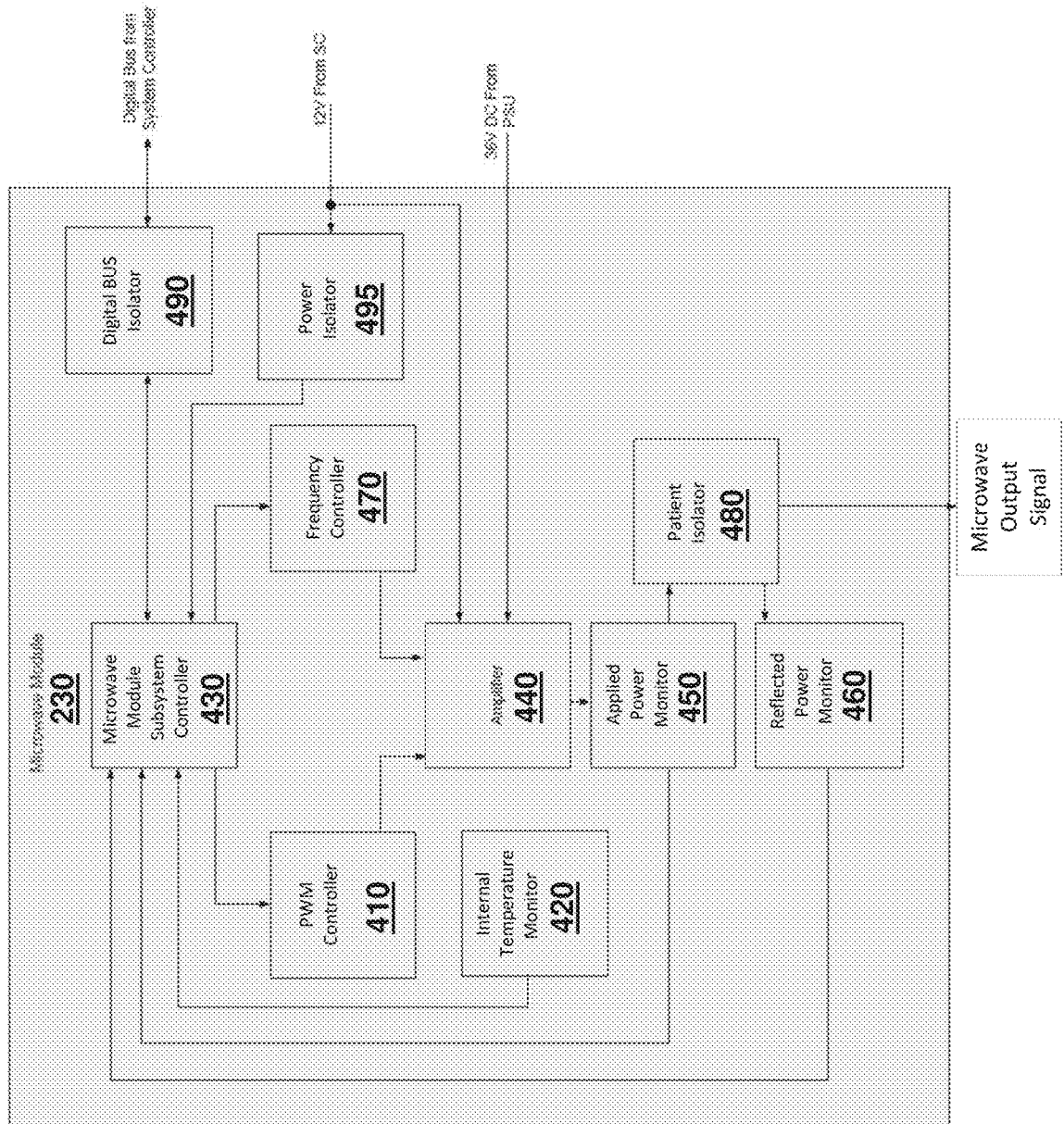
FIG. 4 is a circuit block diagram of a microwave module of the microwave generator of FIG. 2 according to an embodiment of the present disclosure.

FIG. 4 illustrates microwave module 230 of microwave generator 110 according to an embodiment of the present disclosure. Microwave module 230 contains various components including Pulse Width Modulation (PWM) controller 410, internal temperature monitor 420, microwave module subsystem controller 430, amplifier 440, applied power monitor 450, reflected power monitor 460, patient isolator 480, digital bus isolator 490, and power isolator 495. Microwave module subsystem controller 430 receives power, e.g., 12 VDC with a maximum power draw of 350 W, from generator controller 220 through power isolator 495. Power isolator 495 isolates the power supplied to microwave module subsystem controller 430 from generator controller 220.

Microwave module subsystem controller 430 is a programmable processor configured through flash programming, or through other suitable programming methods and languages, to produce up to, for example, 150 W, according to a setting set by a user, and maintain the power setting within, for example, a −5% to +20% range. Microwave module subsystem controller 430 is configured with interlock state settings pertaining to power, current, voltage, temperature, or any other measurable standard suitable for protecting microwave module 230. If an interlock is exceeded, the microwave module subsystem controller 430 may cease the supply of power to any or all components included in microwave module 230.

Microwave module subsystem controller 430 may be calibrated, through software calibration methods including radix-based digital self-calibration, background equivalent radix extraction, interference cancelling, or hardware calibration methods including the use of, for example, comparator/DAC combinations, digitally controllable low-pass filters using a digital potentiometer, and calibration-multiplexers, or any combination of hardware and software solutions, to improve the digital communications links.

Power is received by power isolator 495 from generator controller 220. Power isolator 495 is similar to power isolator 310, which includes one or more transformers, one or more optocouplers, or other suitable circuitry for electrically isolating microwave module 290 from the other modules and circuitry of the microwave ablation system 100. Power isolator 495 provides power to a microwave module subsystem controller 430. In some embodiments, the power isolator 495 may also provide power to amplifier 440.

Internal temperature monitor 420 continually measures the temperature of amplifier 440. Internal temperature monitor 420 may employ a thermocouple, a thermistor, or other suitable temperature sensor. Internal temperature monitor 420 further transmits temperature data to microwave module sub system controller 430. Microwave module sub system controller 430 routes amplifier 440 temperature data through digital bus isolator 490 to generator controller 220 as a value in, for example, degrees Celsius. While monitoring temperature of amplifier 440, internal temperature monitor 420 may cause a cooling system to redistribute and remove heat generated by amplifier 440.

PWM controller 410 generates a pulse width controlled power signal according to instructions from microwave module subsystem controller 430. Frequency controller 470 generates a frequency controlled power signal according to instructions from microwave module subsystem controller 430. Amplifier 440 receives a Pulse Width Modulation (PWM) signal from PWM controller 410, a frequency control signal from frequency controller 470, and power, e.g., 36 VDC with a maximum power draw of 350 W, from power supply unit 210. Using the power from the power supply unit, amplifier 440 amplifies the PWM signal and changes the frequency of the PWM signal according to the frequency control signal to produce a microwave signal. The power signal is provided to patient isolator 480 through applied power monitor 450. Applied power monitor 450 determines the power, voltage, current, and waveform of the microwave signal and communicates the information with microwave module subsystem controller 430 to allow microwave module subsystem controller 430 to recalibrate the microwave signal.

At patient isolator 480, the patient is isolated from the microwave module power source. Patient isolator 480 may include, for example, one or more transformers. Patient isolator outputs a microwave signal to instrument 180.

Reflected power monitor 460, connected to patient isolator 480, monitors the reflected return signal. Reflected power monitor 460 can measure voltage, current, power, and/or impedance. Information determined at reflected power monitor 460 is communicated with microwave module subsystem controller 430, where it allows microwave module subsystem controller 430 to calibrate the microwave signal. Microwave module subsystem controller 430 may compare information from reflected power monitor 460 and applied power monitor 450 to determine the loss and phase shift between incident and reflected waves of the microwave signal. Additionally, microwave module subsystem controller 430 may communicate raw data or processed data through digital bus isolator 490, which is configured, using a transformer or other isolation device, to electrically isolate microwave module sub system controller 430 from other modules connected to the digital bus.

Figure 5:
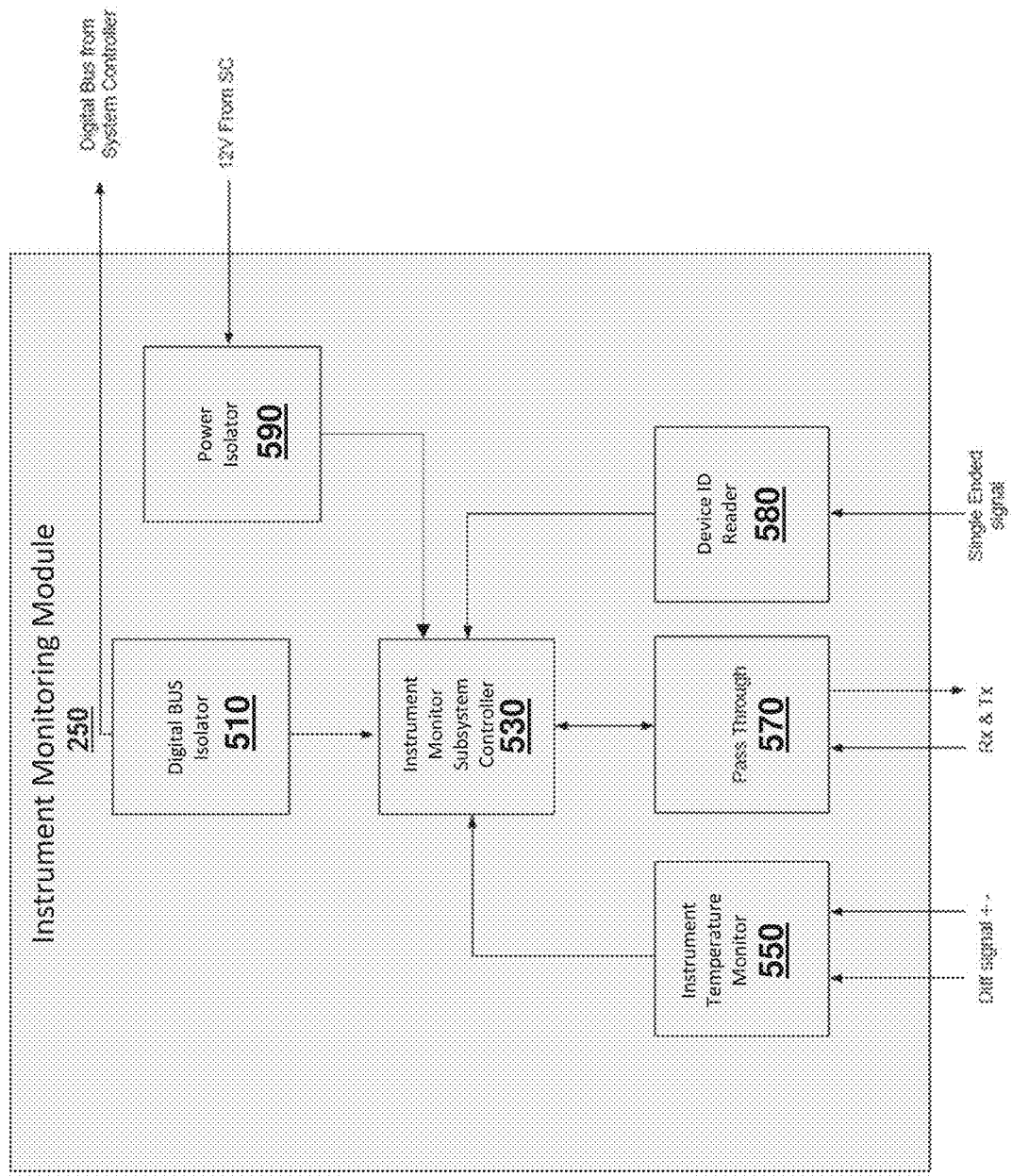
FIG. 5 is a circuit block diagram of an instrument monitoring module of the microwave generator of FIG. 2 according to an embodiment of the present disclosure.

FIG. 5 is a circuit block diagram of instrument monitoring module 250 of microwave generator 110 according to an embodiment of the present disclosure. Instrument monitoring module 250 includes digital bus isolator 510, power isolator 590, instrument monitoring subsystem controller 530, instrument temperature monitor 550, pass through circuit 570, and device ID reader 580. Power isolator 590 is similar to power isolator 310, which includes one or more transformers, one or more optocouplers, or other suitable circuitry for electrically isolating the user interface module 290 from the other modules and circuitry of the microwave ablation system 100. The power isolator 680 provides power to instrument monitor subsystem controller 530.

Instrument monitor subsystem controller 530, controls and communicates with instrument temperature monitor 550, pass through circuit 570, and device ID reader 580. Instrument monitor subsystem controller 530 also communicates with generator controller 220 through a digital bus connected to digital bus isolator 510, which relays a communication signal while electrically isolating instrument monitor sub system controller 530.

Upon startup or at any time as requested by the generator controller or by a user, instrument monitor subsystem controller 530 may instruct device ID reader to receive from device ID memory 170 the device ID of instrument 180 via reusable cable 160. Device ID memory 170 may alternatively be a resistor. Device ID reader 580 may receive a single-ended signal. Data from the received signal is then communicated to instrument monitor subsystem controller 530 for processing and communication to generator controller 220.

Upon starting a procedure, instrument monitor subsystem controller 530 instructs instrument temperature monitor 550 to begin monitoring a temperature of the instrument. The instrument temperature monitor 550 determines a voltage differential across two lines connected with, for example, a thermocouple or thermistor, to determine a temperature of instrument 180.

Pass through circuit 570 receives a microwave output signal through the receive (Rx) channel and outputs the same microwave output signal through the transmit (Tx) channel unchanged or at least with minor changes. Pass through circuit 570 measures voltage and current waveforms and transmits the waveform information to instrument monitor subsystem controller 530. Instrument monitor subsystem controller 530 analyzes the data and transmits the information to generator controller 220 via the digital bus and digital bus isolator 510.

Another aspect of the present disclosure is the use of the radiometer 150. The radiometer 150 detects emissions from materials such as tissue, for example. The emissions detected by the radiometer 150 both before and after application of microwave energy can be sampled and converted to either an analog voltage or a digital signal and forwarded to the instrument monitor subsystem controller 530. FIG. 1 depicts the radiometer 150 as being a separate component of the system. However, this functionality can be implemented directly in the instrument monitor subsystem controller 530 analyzing the signals on the pass through circuit 570.

With this information, the instrument monitor subsystem controller 530 may change or alter or modify or adjust the energy delivered by the microwave generator 110 based on the tissue characteristics encountered by the instrument 180. For example, when the tissue contacted by the instrument 180 and sensed by the radiometry detector or radiometer 150 is healthy tissue, the instrument monitor subsystem controller 530 may prevent microwave generator 110 from applying energy to the tissue. On the other hand, as the instrument 180 approaches tumorous tissue, the instrument monitor subsystem controller 530 may prompt the microwave generator 110 to transmit energy to cauterize the tumorous tissue. The detection of the tumorous tissue (or healthy tissue) may be enabled by first transmitting from the microwave generator 110 through the instrument 180 a non-therapeutic signal (e.g., very low power or duration) at the tissue in question and evaluating the emitted response to the interrogation. The instrument monitor subsystem controller 530 can then employ algorithms and protocols to ascertain the type of tissue and present these results to the user via a connected display or an output on the microwave generator 110.

Further, by continuing to detect the change in the radiometry reading during the application of energy, the instrument monitor subsystem controller 530 can make determinations regarding the cessation, or the sufficiency of the treatment of the tumorous tissue. The detected permit the instrument monitor subsystem controller 530 to adjust operations of the microwave generator 110 based on the feedback received from the instrument 180. Detection of radiometry enables detection of heating of the tissue by detecting electromagnetic waves of a frequency and signal strength emitted by the tissue indicating tissue temperature. Preferably the radiometer 150 operates at a frequency in the microwave range.

Figure 6:
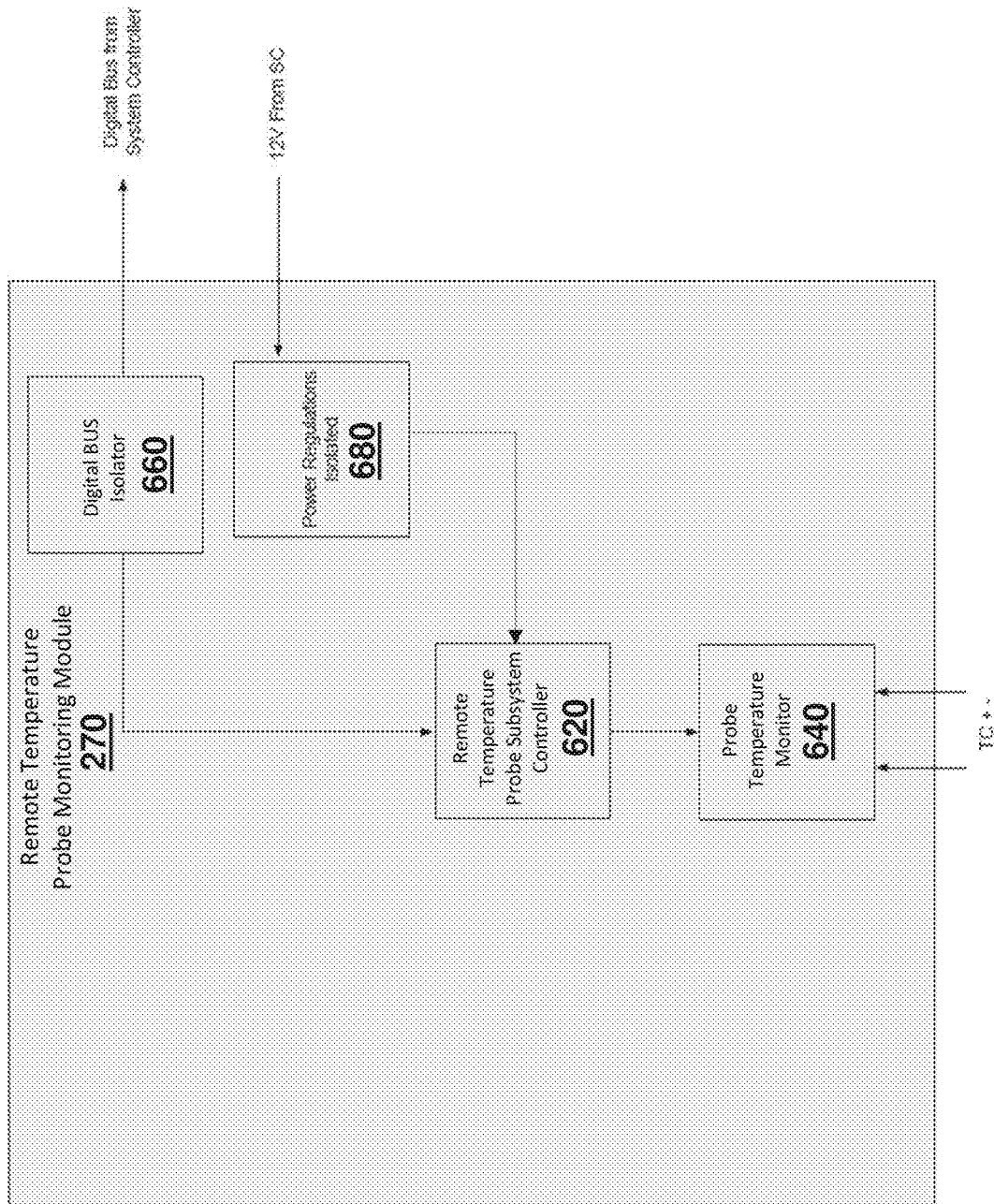
FIG. 6 is a circuit block diagram of a remote temperature probe monitoring module of the microwave generator of FIG. 2 according to an embodiment of the present disclosure.

FIG. 6 illustrates remote temperature probe monitoring module 270 of microwave generator 110 according to an embodiment of the present disclosure. Remote temperature probe monitoring module 270 receives power, e.g., 12 VDC with a maximum power draw of 350 W, from generator controller 220 through power isolator 680. Power isolator 680 is similar to power isolator 310, which includes one or more transformers, one or more optocouplers, or other suitable circuitry for electrically isolating the user interface module 290 from the other modules and circuitry of the microwave ablation system 100. The power isolator 680 provides power to the temperature probe subsystem controller 620.

Temperature probe subsystem controller 620 communicates with and controls probe temperature monitor 640. Temperature probe subsystem controller 620 also communicates with generator controller through a digital communications bus connected to digital bus isolator 660 which electrically isolates temperature probe subsystem controller 620 from the other circuitry and modules in the microwave generator 110. The digital bus isolator 660 may include a capacitor or other isolation component or barrier, a transmitter to couple a communication signal into one side of the isolation component, and a receiver to convert the signal on the other side of the isolation component into a digital signal. The digital bus isolator 660 may include multiple isolation components, transmitters, and receivers to allow for bidirectional communication between the temperature probe subsystem controller 620 and the generator controller 220.

Upon starting a procedure, instrument monitor subsystem controller 530 of the instrument monitoring module 250 may instruct probe temperature monitor 640 of the remote temperature probe monitoring module 270 to begin monitoring a temperature of remote temperature probe 190. Remote temperature probe 190 is placed at or near an ablation site to monitor tissue temperature. The temperature at the site is then measured by a temperature sensor of the remote temperature probe 190, such as a thermocouple or thermistor. The instrument temperature monitor 550 may measure the temperature by measuring a voltage differential across two lines connected to the temperature sensor within remote temperature probe 190.

Figure 7:
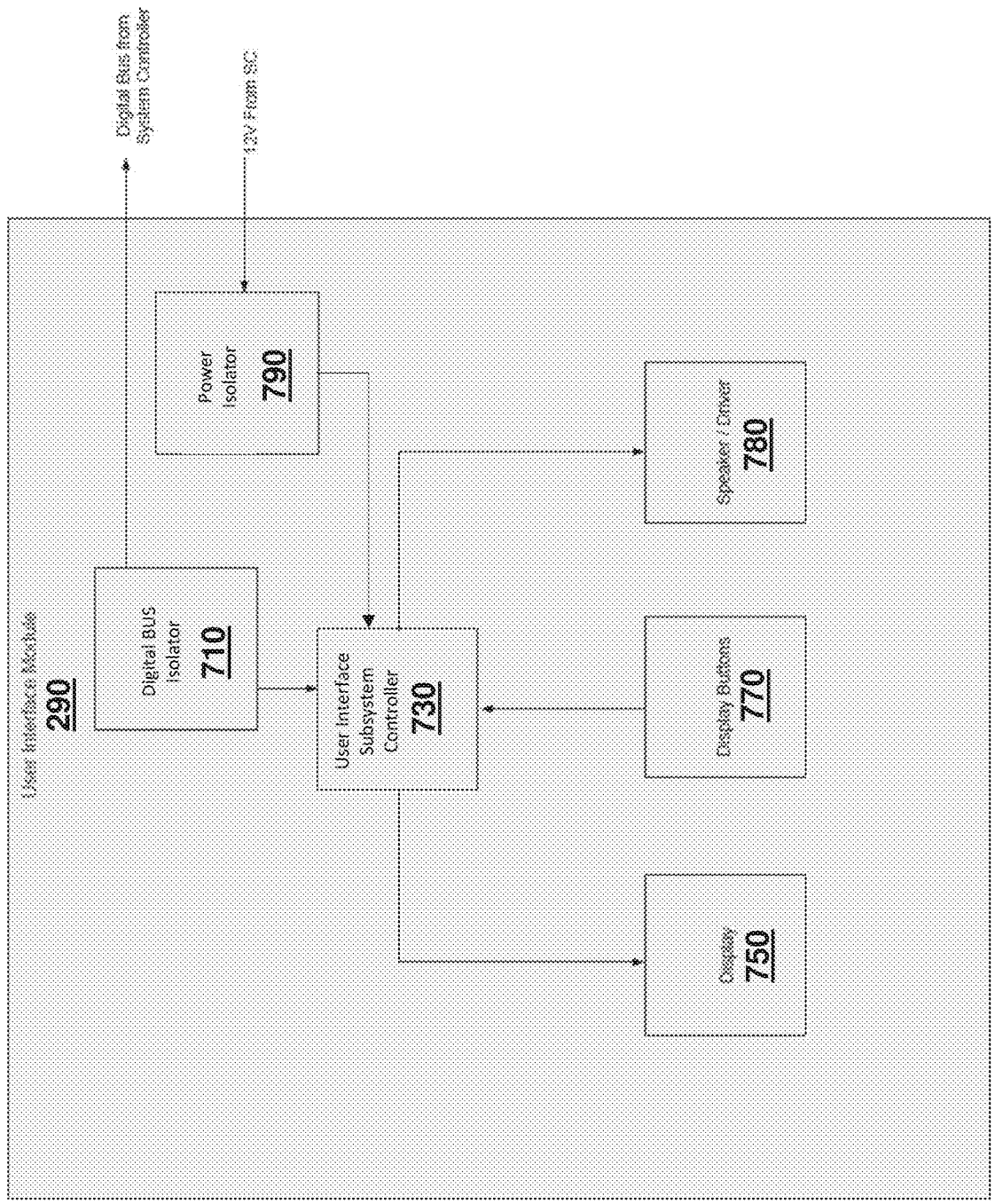
FIG. 7 is a circuit block diagram of a user interface module of the microwave generator of FIG. 2 according to an embodiment of the present disclosure.

FIG. 7 illustrates user interface module 290 of microwave generator 110 according to an embodiment of the present disclosure. User interface module 290 includes power isolator 790, digital bus isolator 710, user interface subsystem controller 730, display 750, display buttons 770, and speaker/driver 780. Power isolator 790 is similar to power isolator 310, which includes one or more transformers, one or more optocouplers, or other suitable circuitry for electrically isolating the user interface module 290 from the other modules and circuitry of the microwave ablation system 100. The power isolator 790 provides power to the user interface sub system controller 730.

User interface module 290 controls and communicates with display 750, display buttons 770, and speaker/driver 780. Display 750 is any suitable device configured to display information to a user, including, but not limited to, a Light-Emitting Diode (LED) display, a Liquid Crystal Display (LCD), or an Organic Light-Emitting Diode (OLED) display. User interface subsystem controller 730 receives information from generator controller 220 regarding settings and condition of the system as well as status and data from other modules. User interface subsystem controller 730 further receives user input from display buttons 770 or other suitable user controls. User interface subsystem controller 730 transmits the information regarding the system and/or user inputs to display 750 and causes display 750 to display, to a physician or operator, the current state of the generator, selected settings, indicators of warnings or errors, a navigable interface, and/or other information that would be useful to a physician or operator during a microwave ablation procedure.

Display buttons 770 enable a physician or an operator to select options displayed on display 750. By manipulating display buttons 770, a physician or operator may set thresholds, including those for voltage, temperature, impedance, and/or current. A physician or operator may further manipulate display buttons 770 to set a desired microwave signal, to adjust the microwave signal, to set a time for microwave signal application, or to start and stop microwave signal generation.

Speaker/driver 780 produces an audio signal to provide status information to a physician or operator. The audio signal may inform the physician or operator that generator controller 220 has determined an error. Generator controller 220 may transmit error information to user interface subsystem controller 730, which generates an audio signal indicative of an error and transmits it to speaker/driver 780. Additionally, user interface subsystem controller 730 may cause speaker/driver 780 to produce audio signals to indicate that microwave signal application has begun or ended.

Figure 8:
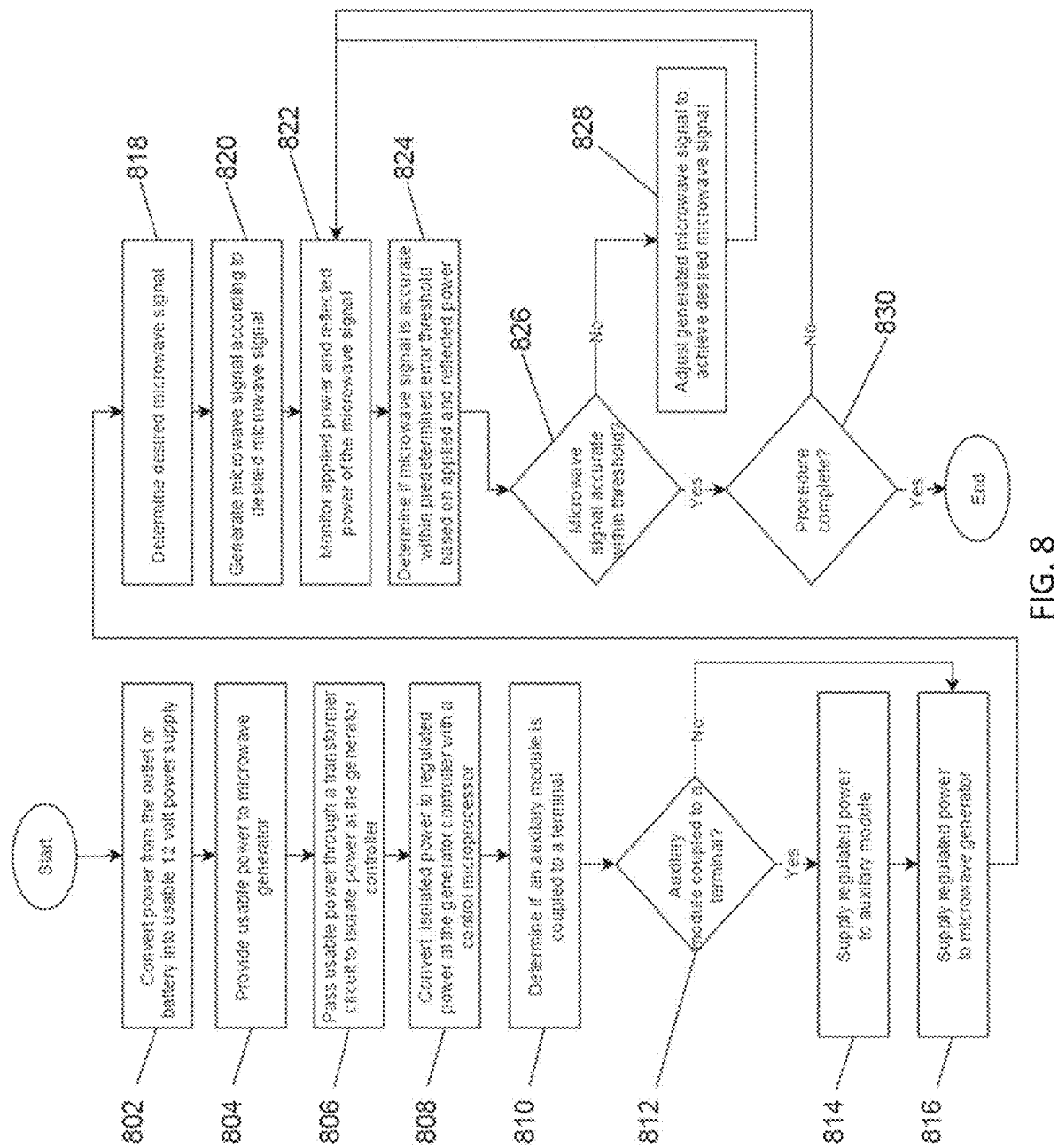
FIG. 8 is a flowchart illustrating a method for operating a microwave generator and monitoring application of the microwave signal.

FIG. 8 is a flowchart illustrating a method for generating a microwave signal and monitoring an instrument applying the microwave signal, according to one embodiment. Power is applied to the generator through, for example, a battery or a wall outlet. The received power is converted, at step 802, to a useable power supply, such as a 12 VDC supply. At steps 804 the useable power is provided to microwave module 230. At step 806, the useable power passes through a power isolator 310 including a transformer at generator controller 220, providing isolated power to be used at the controller board of generator controller 220. At step 808, generator controller microprocessor 330 receives the isolated power and generates regulated power to be provided to other components or modules.

At step 812, it is determined whether an auxiliary module is coupled to a terminal of the microwave generator. Generator controller microprocessor 330 may send a query signal to the terminals or monitor for a draw of power from the terminals to determine if an auxiliary module is coupled to a terminal. In the alternative, the auxiliary modules, such as those described in FIGS. 5-7, may send a signal indicating their presence. If an auxiliary module is determined to be coupled to a terminal, the process proceeds to step 814 where regulated power is supplied to any auxiliary modules coupled to the terminals of the microwave generator. If an auxiliary module is determined not to be coupled to a terminal, the process proceeds to step 816. At step 816, regulated power is supplied to microwave signal generator, such as microwave module 230.

At step 818, a desired microwave signal is determined according to, for example, a user input, a factory setting, or a tool specification. At step 820, the microwave generator generates a microwave signal according to the desired microwave signal and supplies the microwave signal to an instrument to perform a microwave ablation procedure. While the procedure takes place, microwave module 230 monitors the microwave signal applied to the instrument and receives and monitors a reflected power signal from the instrument. Microwave module 230 may store and process the information locally or transmit the information via the communications bus to generator controller 220. At step 824, microwave module 230 or generator controller 220 analyzes the applied microwave signal and the reflected microwave signal, compares the applied microwave signal and the reflected microwave signal, and determines whether the comparison or the individual signals are within predetermined thresholds for determining successful and accurate application of the microwave signal.

At step 826, if it is determined that the microwave signals are not within predetermined thresholds, the process continues to step 828 where the generated microwave signal is adjusted by microwave module 230, optionally after receiving an instructive signal from generator controller 220. Once the microwave signal has been adjusted, the process returns to repeat steps 822 through 826.

If, at step 826, it is determined that the microwave signals are within predetermined thresholds, the method proceeds to step 830 where it is determined whether the procedure has been completed, determined through, for example, a timer or a user's decision to end the procedure. If it is determined that the procedure is not complete, steps 822 through 830 are repeated until the procedure is complete. If it is determined that the procedure is complete, the process ends.

Figure 9:
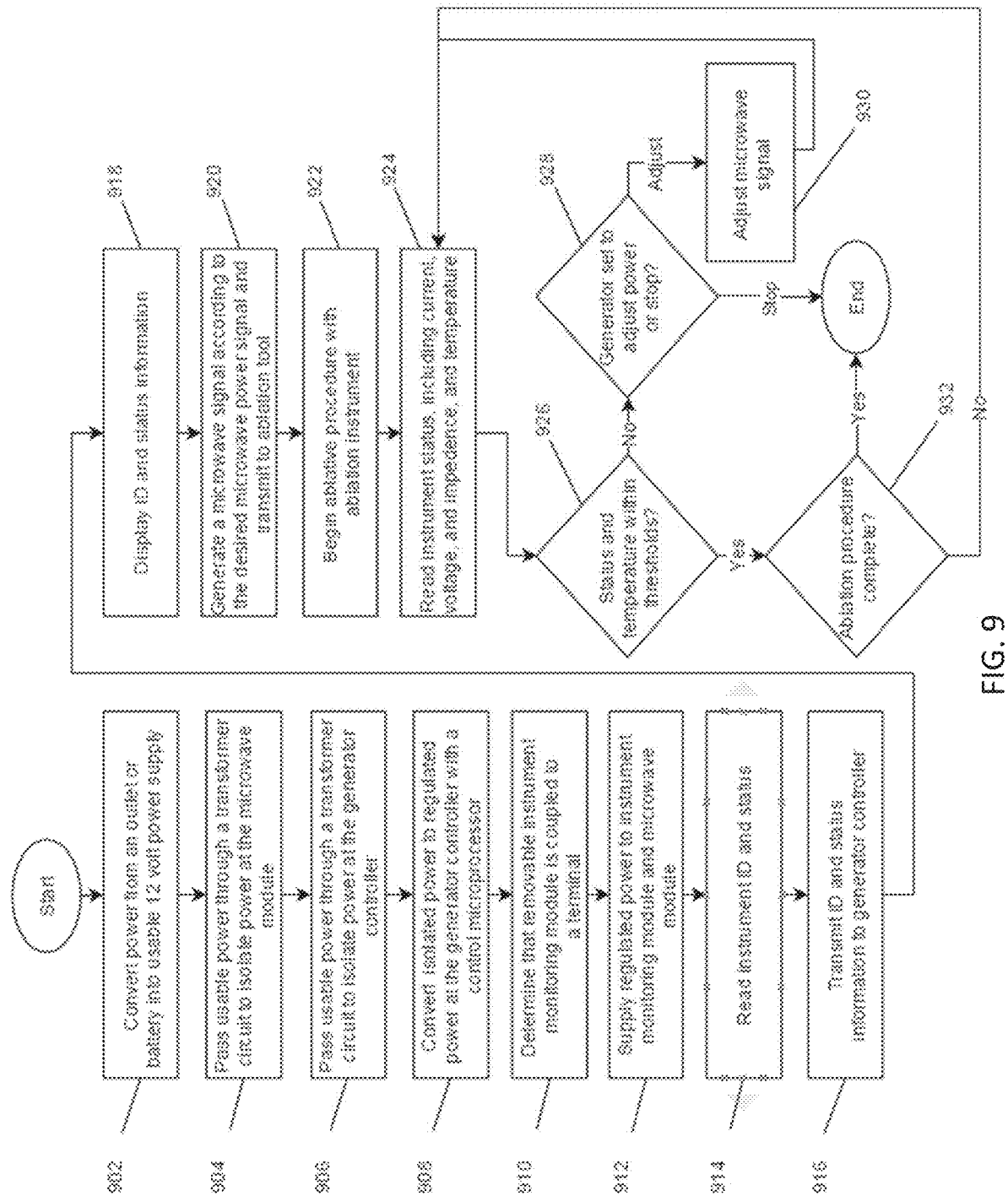
FIG. 9 is a flowchart illustrating a method for generating a microwave signal and monitoring an instrument applying the microwave signal.

FIG. 9 is a flowchart illustrating a method for generating a microwave signal and monitoring an instrument applying the microwave signal, according to one embodiment. At the outset, a physician or operator determines which removable modules or circuits are required for the surgical procedure. If the operator determines that the instrument contains identification information and is designed to provide status information, the operator may choose to couple instrument monitoring module 250 to microwave generator 110. The instrument monitoring module 250 is coupled to microwave generator 110 by, for example, plugging instrument monitoring module 250 into a terminal or port of microwave generator 110. In some embodiments, the terminals or ports of microwave generator 110 include apertures or holes configured to receive pins of instrument monitoring module 250 and create a friction fit. The microwave generator is then connected to a power source such as an outlet, a battery, or any other suitable source of sustained power suitable for completing a microwave surgical procedure.

At step 902, power supply unit 210 draws power from the power source and converts the power to a lower, useable level, for example, 12 V, capable of powering microwave generator controller 220 and microwave module 230. At steps 904 and 906, the converted power is provided to microwave module 230 and microwave generator controller 220. In the generator controller 220, the converted power passes through a power isolator such as a transformer in order to provide isolated power to the subsystem controllers 330, 430. At step 908, microwave generator controller microprocessor 330 generates regulated power.

At step 910, it is determined whether instrument monitoring module 250 is coupled to a terminal connected to generator controller 220. Generator controller 220 sends a query signal to a module upon connection of the module to an available terminal. If the module is instrument monitoring module 250, the module transmits a signal indicating its identity as instrument monitoring module 250 to generator controller 220.

After instrument monitoring module 250 is identified, microwave generator controller microprocessor 330 supplies regulated power to instrument monitoring module 250 and microwave module 230 at step 912.

At step 914, instrument monitoring module 250 queries instrument 180 and determines the device ID and/or status information, including, for example, the number of previous uses of instrument 180. At step 916, instrument monitoring module 250 processes the device ID and/or status information and transmits the device ID and/or status information to microwave generator controller 220 via a digital bus. At step 918, microwave generator controller 220 displays the device ID and/or status information on a display, which the physician or operator can read to determine if the tool is suitable for use. Microwave generator controller 220 determines a desired microwave signal best suited for selected instrument 180 and for the type of procedure carried out by instrument 180.

After the desired microwave power is determined, the surgical procedure is ready to begin. A physician or operator may activate the microwave power generator by entering a user input, by, for example, depressing a foot pedal or selecting an option on a user interface display. The microwave power generator may continue generating microwave power until an end signal is received or until an activate signal ceases to be received. At step 920, microwave module 230 generates the desired microwave signal as instructed by microwave generator controller 220 and provides that microwave signal to instrument 180. At step 922, the surgical procedure begins. The surgical procedure may include applying microwave power to target tissue in order to ablate the target tissue. At step 924, instrument monitoring module 250 reads status information, including temperature, voltage, current, and/or impedance, from instrument 180 and determines if the status information exceeds predetermined status thresholds at step 926. Determining whether a threshold has been exceeded may occur at microwave module 230 and the determination may be sent to microwave generator controller 220, or microwave module 230 may transmit the status information to microwave generator controller 220 for microwave generator controller 220 to determine whether a threshold is exceeded.

If the tool status is not within a predetermined threshold, the process proceeds to step 928. At step 928, microwave generator controller 220 determines how to react to an out of threshold status. If the microwave generator is programmed to halt the application of microwave power when a threshold has been exceeded, the process ends. If the microwave generator controller 220 is programmed to adjust the microwave signal, the process proceeds to step 836 at which the microwave signal is adjusted so that the procedure may continue.

If the tool status is within a predetermined threshold, the procedure continues to step 932. At step 932, it is determined whether the procedure is complete. The determination is made by a physician or operator or by microwave generator 110 according to predetermined goals, such as the achievement of a predetermined ablative zone. If the procedure is not complete, the process returns to step 924. If the procedure is complete, the process ends.

Figure 10:
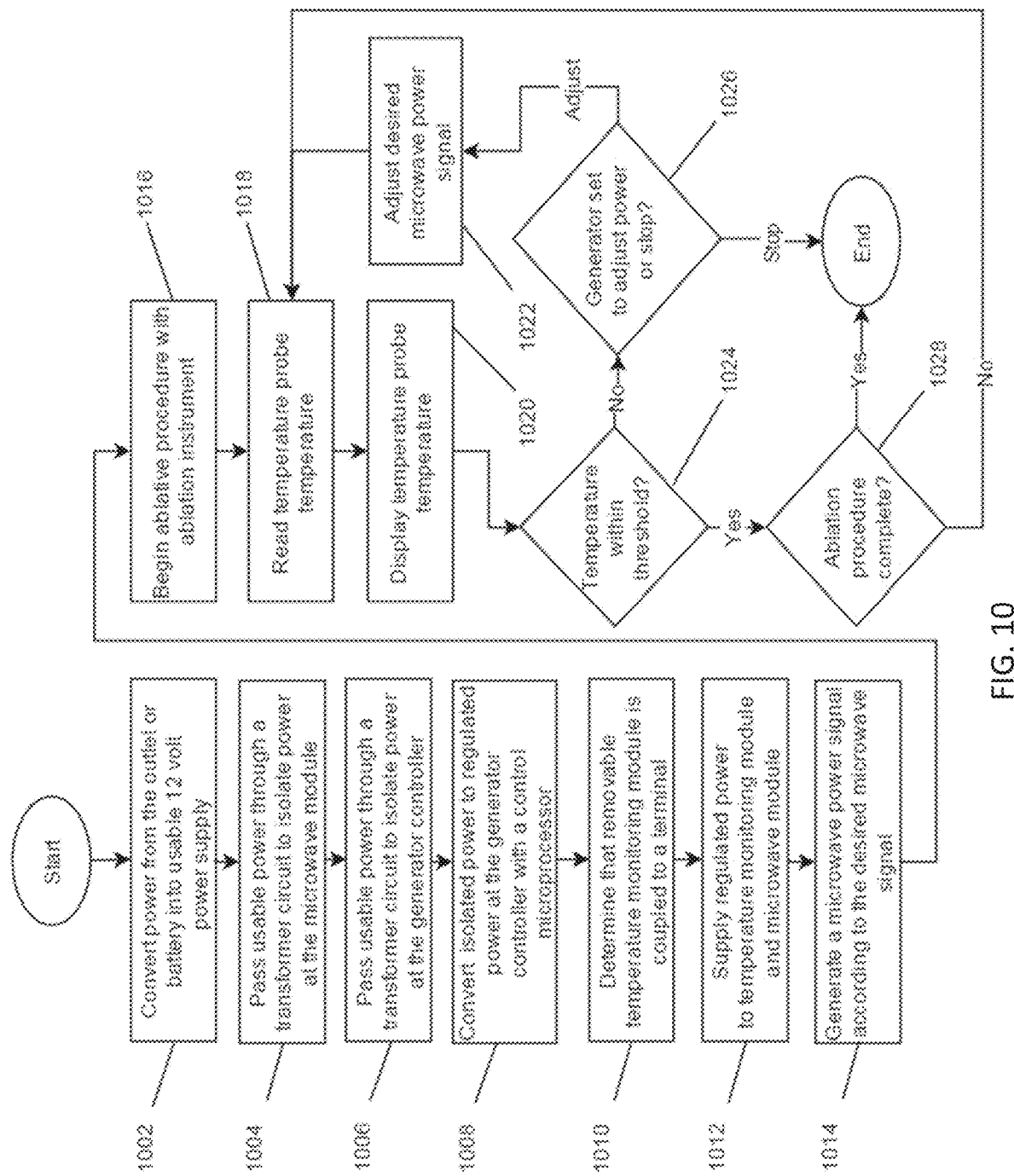
FIG. 10 is a flowchart illustrating a method for generating a microwave signal while monitoring temperature at a temperature probe.

FIG. 10 is a flowchart illustrating a method for generating a microwave signal while monitoring temperature at a temperature probe, according to one embodiment. At the outset, a physician or operator determines which removable modules are required for the surgical procedure to be performed. If the operator determines that remote temperature probe 190 is required, the physician or operator chooses to couple remote temperature probe monitoring module 270 to microwave generator 110. The remote temperature probe monitoring module 270 maybe be removably coupled to microwave generator 110 by, for example, plugging remote temperature probe monitoring module 270 into a port or terminal within microwave generator 110. In some embodiments, the ports within microwave generator 110 include apertures or holes configured to receive pins of remote temperature probe monitoring module 270 and create a friction fit. The microwave generator is connected to a power source such as an outlet, a battery, or any other suitable device for providing sustained power suitable for completing a microwave surgical procedure.

At step 1002, power supply unit 210 draws power from the power source and converts it to a lower, useable level, for example, 12 volts, capable of powering microwave generator controller 220 and microwave module 230. At steps 1004 and 1006, the converted power is provided to microwave module 230 and microwave generator controller 220 where it passes through a transformer circuit in order to provide isolated power to the subsystem controllers 330, 430. At step 1008, microwave generator controller microprocessor 330 generates regulated power. The generated regulated power is use to power various generator modules and provided power for a bus providing communication among modules and various ports and/terminals.

At step 1014, microwave generator controller microprocessor 330, using the bus, queries the various terminals to determine if a removable module is coupled to any of the terminals. Microwave generator controller microprocessor 330 receives a response signal from remote temperature probe monitoring module 270 via the bus indicating that remote temperature probe monitoring module 270 is coupled to a port and initiating a connect for supplying power to remote temperature probe monitoring module 270. At steps 1012 and 1014, regulated power is provided, via the bus, to remote temperature probe monitoring module 270 and microwave module 230.

After a desired microwave signal is determined, the surgical procedure is ready to begin. A physician or operator may activate the microwave signal generation by entering a user input, by, for example, depressing a foot pedal. When a start signal is received, generator controller 220 controls microwave module 230, at step 1014, to generate the desired microwave signal and transmit it to instrument 180. In some embodiments, the generator controller 220 performs a small portion of the control functions for generating a microwave signal while the microwave module 230 performs the majority of the control functions.

At step 1016, the procedure begins. The procedure may include applying microwave power to target tissue in order to ablate the target tissue. At step 1018, remote temperature probe monitoring module 270 reads a tissue temperature at the location of remote temperature probe 190 and transmits the reading to generator controller microprocessor 330. The determined tissue temperature is displayed on a display at step 1020.

At step 1022, generator controller 220 or remote temperature probe monitoring module 270 determines whether a tissue temperature threshold has been exceeded. If the threshold is exceeded, the process proceeds to step 1024 where it is determined whether microwave generator 110 is set to adjust the output microwave power or stop the application of the output microwave power. If microwave generator 110 is set to stop output microwave power, the process ends. If microwave generator 110 is set to adjust the output microwave power, the output microwave power is adjusted at step 1026 and the process returns to step 1018.

If the temperature is within the threshold at step 1024, the process continues to step 1030. At step 1030, microwave generator 110, a physician, or an operator determines whether the procedure is complete. If the procedure is determined to be complete, the process ends. If the procedure is determined not to be complete, the process returns to step 1018. Steps 1018-1028 are repeated until microwave generator 110, a physician, or an operator determines that the procedure is complete.

Figure 11:
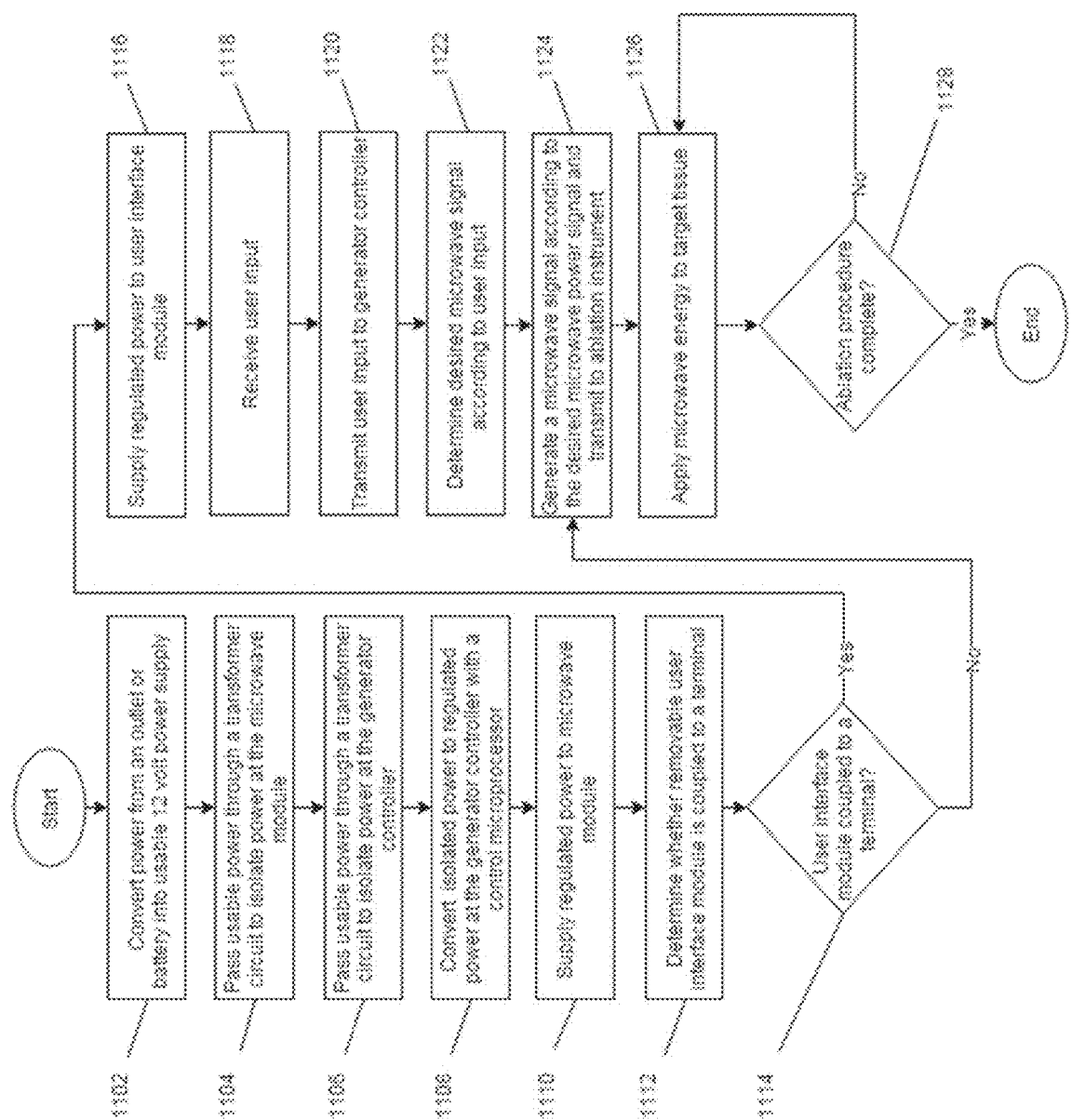
FIG. 11 is a flowchart illustrating a method for generating a microwave signal in response to user inputs.

FIG. 11 is a flowchart illustrating a method for generating a microwave signal in response to user inputs, according to one embodiment. At the outset, a physician or operator determines which removable modules are needed for the surgical procedure to be performed. If the operator determines that a user interface is needed, the operator couples user interface module 290 to the microwave generator 110. The user interface module 290 may be connected to microwave generator 110 by, for example, plugging user interface module 290 into a port or terminal within microwave generator 110, wherein the ports within microwave generator 110 include holes configured to receive pins of instrument monitoring module 250 and create a friction fit. Microwave generator 110 is connected to a power source such as an outlet, a battery, or any other suitable of sustained power suitable for completing a microwave surgical procedure.

At step 1102, power supply unit 210 draws power from the power source and converts the power to a lower, useable level, for example, 12 volts, capable of powering microwave generator controller 220 and microwave module 230. At steps 1104 and 1106, the converted power is provided to microwave module 230 and microwave generator controller 220 where it passes through a transformer circuit in order to provide isolated power to the subsystem controllers 330, 430 for powering microwave generator controller 220 and microwave module 230. At step 1108, microwave generator controller microprocessor 330 generates regulated power which is provided to microwave module 230 at step 1110.

At step 1112, microwave generator controller microprocessor 330, using the bus, queries the various terminals to determine if a removable module is coupled to any of the terminals. If microwave generator controller microprocessor 330 receives a response signal from user interface module 290 via the bus indicating that user interface module 290 is coupled to a port, it is determined that user interface module 290 is coupled to a terminal, at step 1114, if it is determined that user interface module 290 is not coupled to a terminal, the process proceeds to step 1124. If it is determined that user interface module 290 is coupled to a terminal, the process proceeds to step 1116.

At step 1116, a connection is established and regulated power is supplied to user interface module 290 via the bus. The supplied power powers display 750, speaker/driver 780, and enables display buttons 770. Using display buttons 770 or a display 750 touchscreen, the user may enter an input. At step 1118, user interface module 290 receives user inputs from a physician or an operator. Inputs may include power settings, temperature and impedance thresholds, and ablation time. At step 1120, the input information is transmitted from user interface module 290 to generator controller 220 for processing and controlling the system according to the user inputs at step 1118. At step 1122, generator controller 220 determines a desired microwave power according to user inputs.

After the desired microwave power is determined, the surgical procedure is ready to begin. A physician or operator may activate the microwave signal generation by entering a user input, by, for example, depressing a foot pedal. At step 1124, in response to an activation signal, microwave module 230 generates a microwave signal according to the determined desired microwave signal and provides that microwave signal to instrument 180. The microwave signal may continue to be generated until an end signal is received or until the activating signal ceases to be received.

Once the microwave power is generated, the procedure may begin. The procedure may include applying microwave power to target tissue in order to ablate the target tissue. At step 1128, a determination is made, either by an operator or by microwave generator 110, according to predetermined goals, such as the achievement of a predetermined ablative zone or an end of a set period, whether the procedure is complete. If the procedure is not complete, the process returns to step 1126 and the microwave energy continues to be applied to the target tissue. If the procedure is complete, the process ends.

Figure 12:
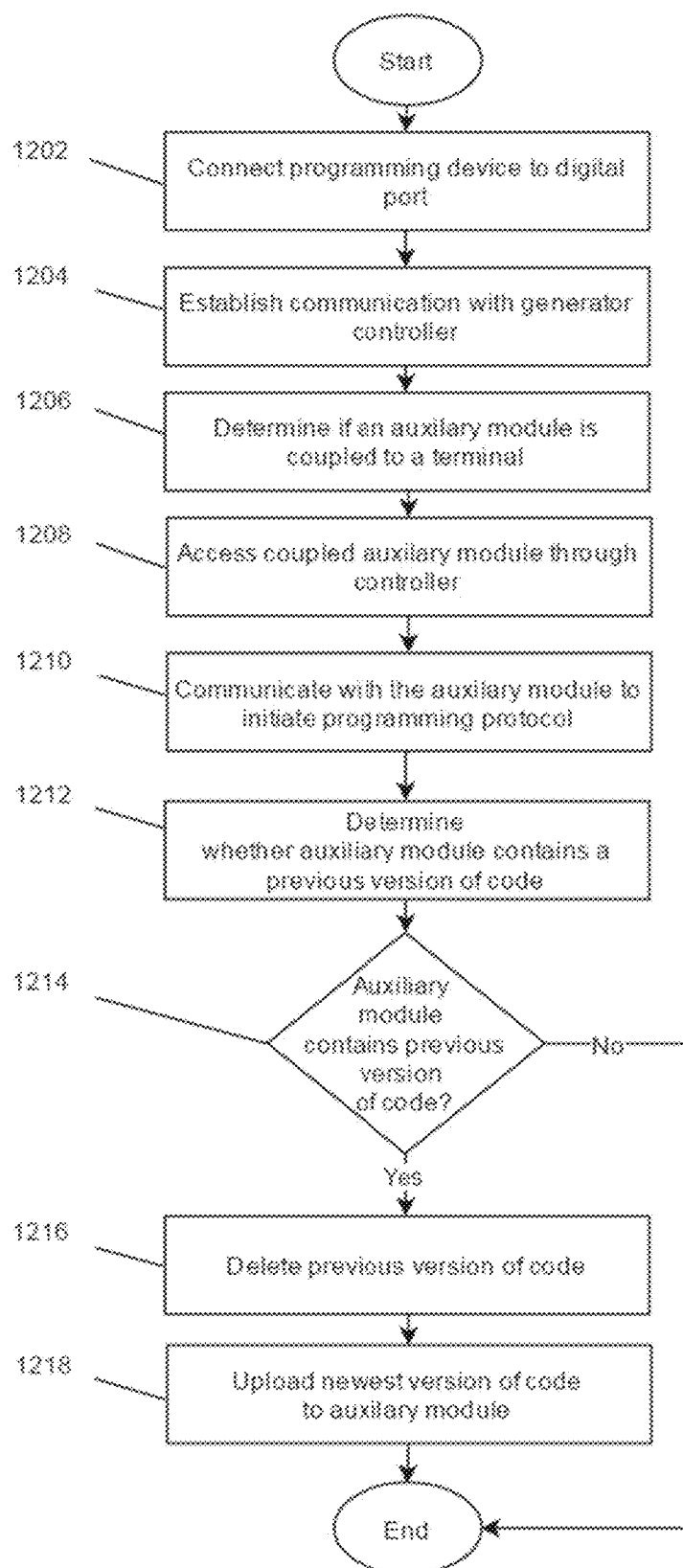
FIG. 12 is a flowchart illustrating a method for programming an auxiliary module through a microwave generator controller.

FIG. 12 is a flowchart illustrating a method for programming an auxiliary module through a microwave generator controller, according to one embodiment. At step 1202, a physician or operator connects an external programming device to digital port 120 using, for example, a USB connector or any other suitable connector. At step 1204, the external programming device and generator controller microprocessor 330, establishes communication. Either the external programming device or generator controller microprocessor 330 may relay an initial request to communicate. After establishing a connection, at step 1206, generator controller microprocessor 330 queries terminals to determine that one or more auxiliary modules are coupled to the terminals. If one or more auxiliary modules are coupled to the terminals, the one or more auxiliary modules will send a signal indicating their presence to generator controller microprocessor 330. Then, generator controller microprocessor 330 may probe the coupled modules to received information to present to a user via the programming device and allow the user to select a module for programming. At step 1212, generator controller microprocessor 330 determines whether the selected module contains a previous version of program code or if the memory lacks program code.

At step 1214, if the selected auxiliary module does not contain a previous version of the code, the process proceeds to step 1218. If the selected specialize module contains previous programming information, controller microprocessor 330 causes the previous programming information to be deleted from a memory of the selected auxiliary module, in step 1216.

At step 1218, generator controller microprocessor 330 allows the external programming device to access the selected module, such as microwave module 230, instrument monitoring module 250, remote temperature probe monitoring module 270, and user interface module 290, through the communication bus. During communication with one of the modules, the external programming device loads code onto the subsystem controller of the selected module. The code loaded may set or update the firmware code for the processor and allows the external device to program the module.

Figure 13:
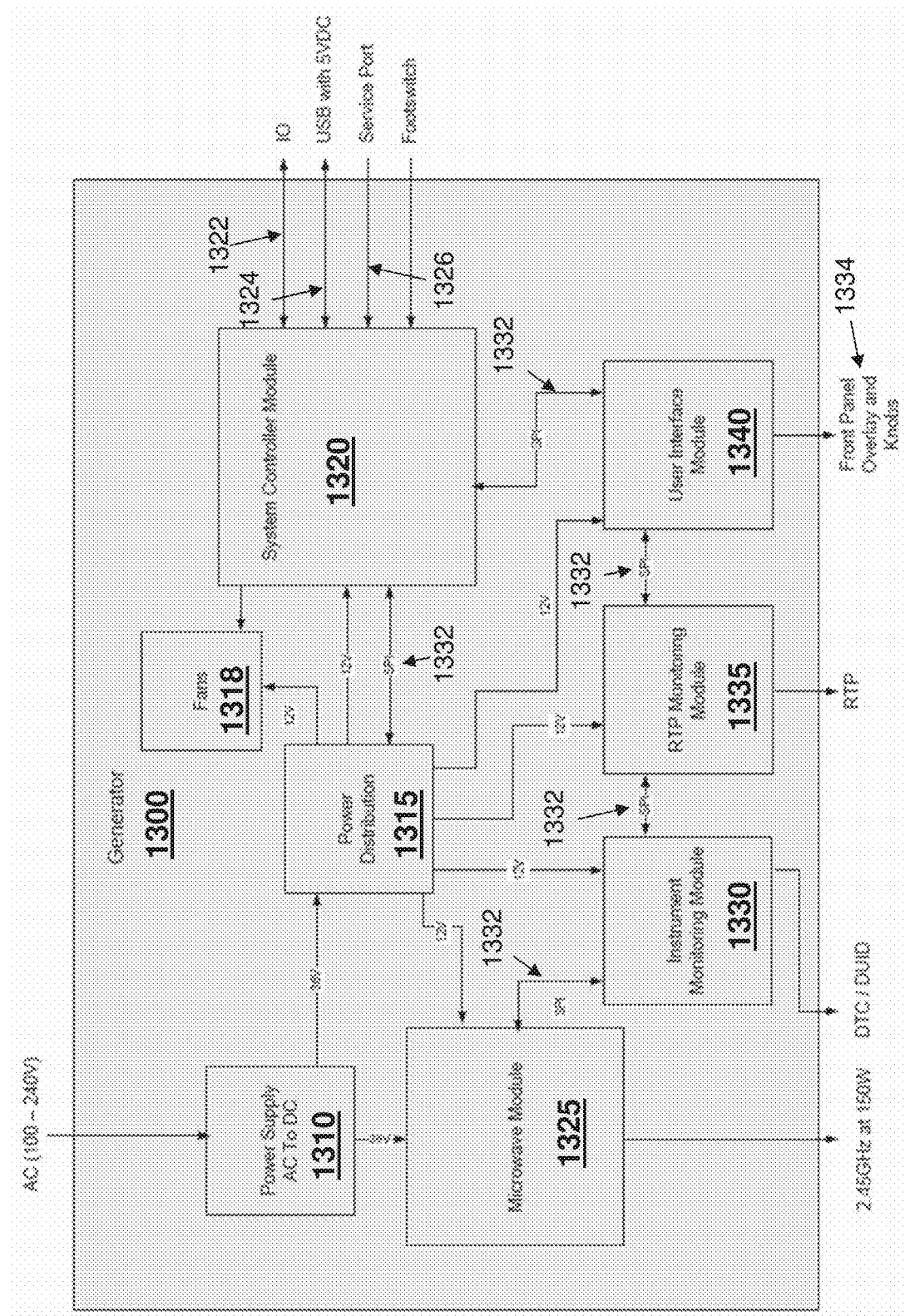
FIG. 13 is a circuit block diagram of the microwave generator of FIG. 1 according to another embodiment of the present disclosure.

FIGS. 13-20 illustrate another embodiment of the microwave generator 110 of FIG. 1. Similar to the microwave generator 110 of FIG. 2, the microwave generator 1300 of FIG. 13 includes microwave module 1325, instrument monitoring module 1330, RTP monitoring module 1335, and user interface module 1340. As shown in the embodiment of FIG. 13, the microwave module 1325 outputs a 2.45 GHz signal at 150 W; although microwave module 1325 may output any microwave signal having a desired frequency and power level. The user interface module 1340 connects to a front panel overlay and knobs disposed on the physical body of the microwave generator 1300.

The microwave generator 1300 of FIG. 13 also includes an AC/DC power supply 1310, a power distribution module 1315, fans 1318, and a system controller module 1320. The power supply 1310 supplies DC power to both the microwave module 1325 and the power distribution module 1315. The power distribution module 1315 generates various DC voltages for powering modules and other circuitry of the microwave module 1325, the instrument monitoring module 1330, the RTP monitoring module 1335, the user interface module 1340, the fans 1318, and the system controller module 1320. The power distribution module 1315 includes power electronics circuitry, such as a buck converter, to convert the DC voltage output from the power supply 1310 to a lower DC voltage that is appropriate for the modules 1320, 1325, 1330, 1335, and 1340, and fans 1318 in the microwave generator 1300. For example, the power distribution module 1315 may step down the voltage output from the power supply 1310 from 36 V to 12 V. The modules 1315, 1325, 1330, 1335, and 1340 are coupled to each other and/or to the system controller module 1320 via a serial peripheral interface bus (SPI Bus) 1332 that is disposed in the microwave generator in the form, for example, of traces of a printed circuit board. In some embodiments, the SPI Bus 1332 connects each of the microwave module 1325, the instrument monitoring module 1330, the RTP module 1335, and the user interface module 1340 to the system controller module 1320 in parallel.

The system controller module 1320 includes an Input/Output (I/O) port 1322, a Universal Serial Bus (USB) port 1324 with a voltage output, e.g., a 5 VDC output, a service port 1326, and a footswitch port to which a footswitch 140 may be connected. In some embodiments, the system controller module 1320 acts as an interface between external devices or computers and the modules of the microwave generator 1300, which may be designed to operate independently of the system controller module 1320.

Many of the modules of the microwave generator 1300 according to the embodiment of FIG. 13 include an FPGA, an isolation block, and a temperature sensor. This allows each of the modules to operate independently and facilitates the modularity of the microwave generator 1300. Thus, for example, the microwave module 1325 may be incorporated into any surgical generator system or microwave generator so long as the surgical generator system or microwave generator provides an appropriate AC/DC power supply.

In embodiments, the microwave generator 1300 having an appropriately-sized chassis may incorporate multiple microwave modules 1325 and multiple respective instrument monitoring modules 1330 that are powered by the AC/DC power supply 1310 and the power distribution module 1315 to form a multi-channel microwave generator system to drive multiple microwave outputs. The microwave generator 1300 may also incorporate multiple RTP monitoring modules 1335 having multiple respective RTP ports 1750.

In embodiments, the system controller module 1330 can act as a "pass through" module so that an external controller or computer can control the microwave module 1325 via the USB connection 1324. A operating mode switch of the service port 1326 may be used to set the microwave generator 1300 to a mode that allows an external computer (not shown) running software with its own user interface to communicate with and control the microwave module 1325. In some embodiments, the operating mode switch may disable the microwave control software in the system controller module 1320 and hand control over to the external computer.

In some embodiments, the system controller module 1320 does not perform the power regulation, but transmits a desired power level to the microwave module 1325. The microwave module 1325 may incorporate its own controller and power regulation circuitry to generate a microwave signal having the desired power level. The system controller module 1320 may run software to determine the parameters of a desired microwave signal, e.g., the duty cycle of microwave pulses or the shape of a microwave pulse, based on data retrieved from the instrument monitoring module 1330 and RTP monitoring module 1335. The system controller module 1320 may then transmit the parameters of the desired microwave signal to the microwave module 1325, which perform control and power regulation to generate microwave signal having the parameters of the desired microwave signal.

Figure 14:
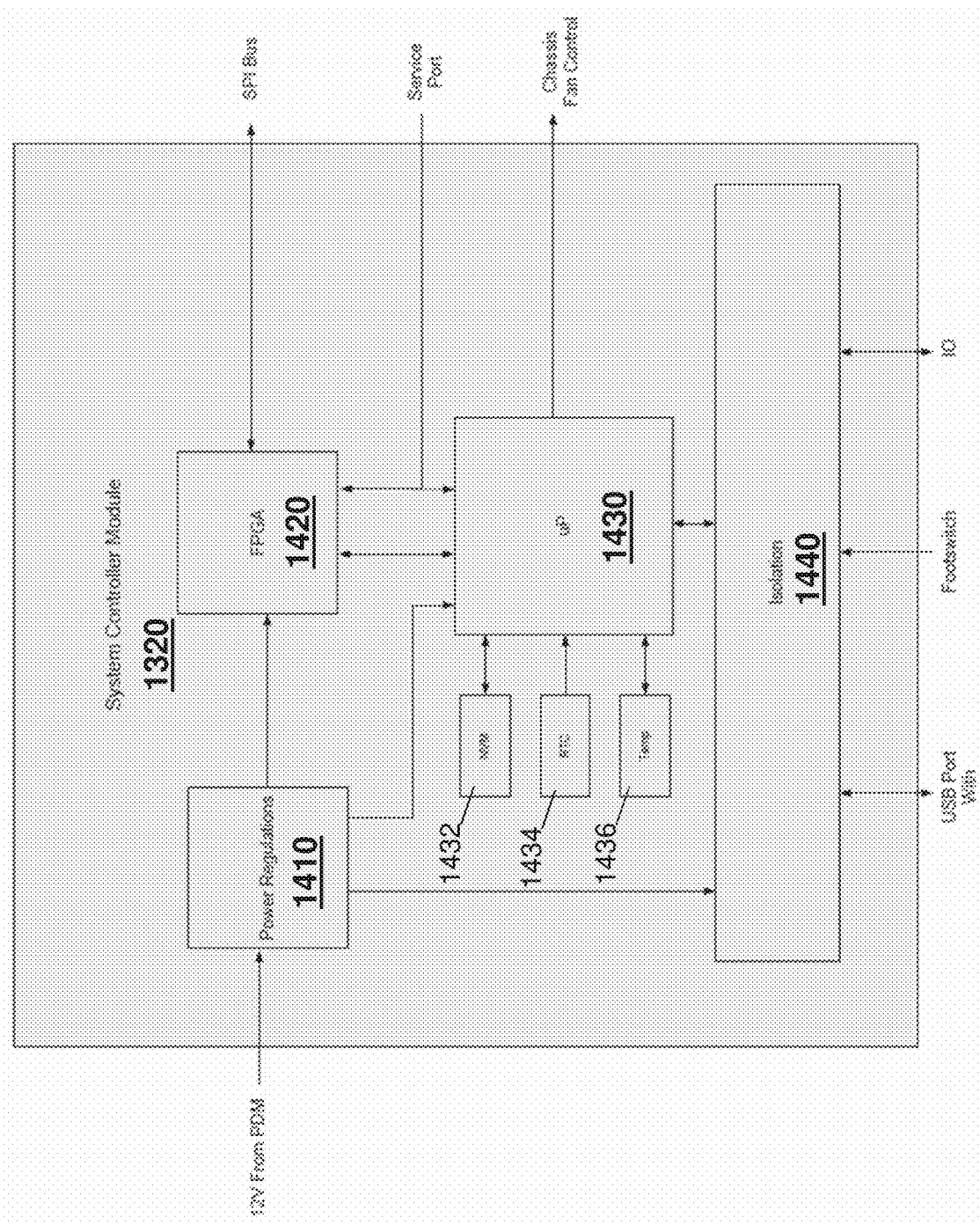
FIG. 14 is a circuit block diagram of a system controller module of the microwave generator of FIG. 13 according to another embodiment of the present disclosure.

FIG. 14 is a circuit block diagram of the system controller module 1320 of the microwave generator 1300 of FIG. 13 according to another embodiment of the present disclosure. The system controller module 1320 includes a power regulation circuit or block 1410 that receives DC power from the power distribution module 1315, a field programmable gate array (FPGA) 1420 connected to the SPI Bus 1332 and the service port 1326, a microprocessor 1430 connected to the FPGA 1420, the service port 1326, and an isolation device 1440 that provides isolation between the internal electronics of the system controller module 1320 and the patient-side connections to the USB port, the footswitch, and the I/O. The system controller module 1320 and the other modules in the microwave generator 1300 include power regulation circuits or blocks, such as power regulation block 1410, to condition the DC power, which is received from the AC/DC power supply 1310 via the power distribution module 1315, for the electronics of the modules.

The FPGA 1420 monitors the SPI Bus 1332 to make sure values, settings, and/or parameters of the other modules, e.g., the power distribution module 1315, are within safe or desired ranges or limits. For example, the FPGA 1420 monitors the packets on the SPI Bus 1332 for in-range parameter values and proper communications. If the parameter values are out of range or the communication rate is not normal, the FPGA 1420 can pull down the SPI Bus 1332, which triggers a failsafe condition within the peripheral modules.

The system controller module 1320 receives input from the service port 1326 and the I/O port 1322 and provides the input to the other modules in the microwave generator 1300. In some embodiments, the system controller module 1320 is a "pass through" module for an external controller (not shown) which is connected to the system controller module 1320 via the SPI Bus 1332. In embodiments, the FPGA 1420 is configured to detect a software failure and shut down the system upon detecting a software failure. In some embodiments, the data obtained by instrument monitoring module 1330 or RTP monitoring module 1335 is provided to the system controller module 1320 via the SPI Bus 1332. The system controller module 1320 may then provide this data to other modules, such as the microwave module 1325. In other embodiments, data obtained by instrument monitoring module 1325 or RTP monitoring module 1335 is provided directly to other modules via the SPI Bus 1332.

The microprocessor 1430 is connected to non-volatile memory 1432, a real-time clock (RTC) 1434, and a temperature sensor 1436. The service port or panel 1326 may include dual in-line package (DIP) switches (not shown) to turn on or off various components or functions of the system controller module 1320. The USB external control/monitoring link and the I/O control lines are located within the service panel. For example, the DIP switches may be used to choose between a linear gain mode and a pulse width modulation mode. As another example, the DIP switches may be used to turn off the FPGA 1420, such as in a case where testing or external control is being performed on the microwave generator 1300. The system controller module 1320 may include ten pin I/O that is used as a binary latch to instruct or set performance of functions performed by the microwave generator 1300.

Figure 15:
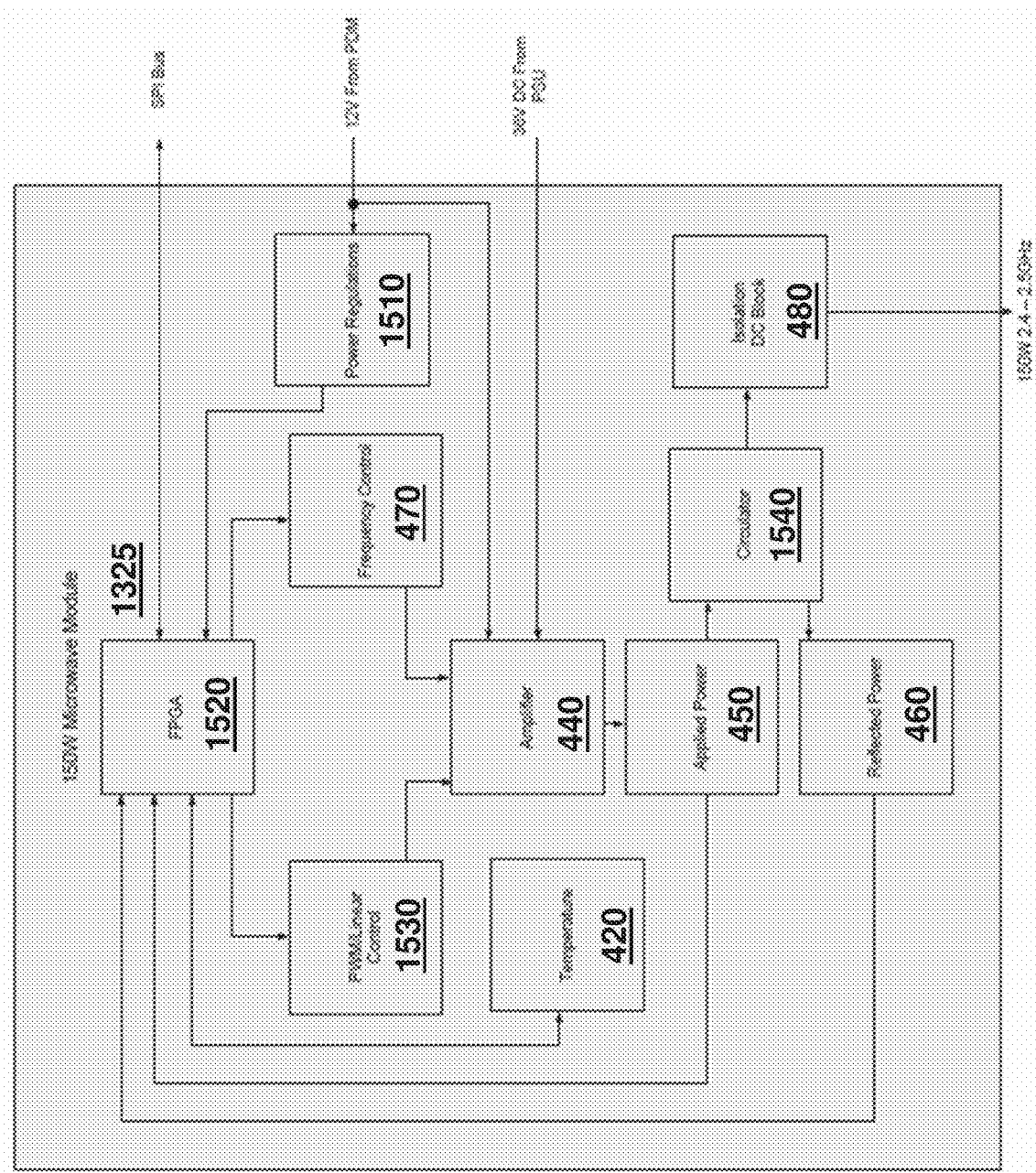
FIG. 15 is a circuit block diagram of a microwave module of the microwave generator of FIG. 13 according to another embodiment of the present disclosure.

FIG. 15 is a circuit block diagram of a microwave module of the microwave generator 1300 of FIG. 13 according to another embodiment of the present disclosure. The microwave module of FIG. 15 includes FPGA 1520 for monitoring the temperature values obtained from the internal temperature monitor 420, power values from the applied power monitor 450, and the power values from the reflected power monitor 460. The FPGA 1520 also provides input to the PWM/linear controller 1530 and the frequency controller 470 to adjust the settings or parameters of the PWM/linear controller 1530 and the frequency controller 470. For example, in embodiments, the FPGA 1520 transmits a signal to the PWM/linear controller 1530 to choose either a PWM control mode or a linear control mode. The FPGA 1520 may receive a command packet on the digital link to configure the power regulation mode as the PWM control mode or the linear control mode. The microwave module also includes a power regulation block 1510 that receives and monitors power provided by the power distribution module 1315 and conditions the power so that it is appropriate for powering the various electronic components of the microwave module 1325.

The microwave module 1325 also includes a circulator 1540 disposed between the isolation DC block and the applied power and reflected power blocks. The circulator 1540 may be a passive non-reciprocal three-port device. The microwave signal from the applied power block may be applied or input to a first port of the circulator 1540 and may be output via a second port of the circulator 1540, which is connected to the DC Isolation block. A reflected microwave signal may then be input to the second port of the circulator 1540 and may be output to the reflected power block via a third port of the circulator 1540. In embodiments, the microwave module 1325 may include the functionality of the other modules and thus may not need to be in communication with the other modules, including the system controller module 1320. In those embodiments, the microwave module 1325 may only need to connect to the power distribution module 1315 via power regulation block 1510 without requiring any communications with the system controller module 1320.

In some embodiments, the microwave module 1325 may bypass the system controller module 1320 and communicate directly with the instrument monitoring module 1330, the RTP monitoring module 1335, and the user interface module 1340 to obtain monitoring data and user input data. In other embodiments, the microwave module 1325 may communicate with the system controller module 1320 only to obtain monitoring data and the user input data stored in the system controller module 1320. In yet other embodiments, system controller module 1320 may transmit high-level control commands to the microwave module 1325. Those high-level control commands may be determined or generated based on the monitoring data and the user input data.

Figure 16:
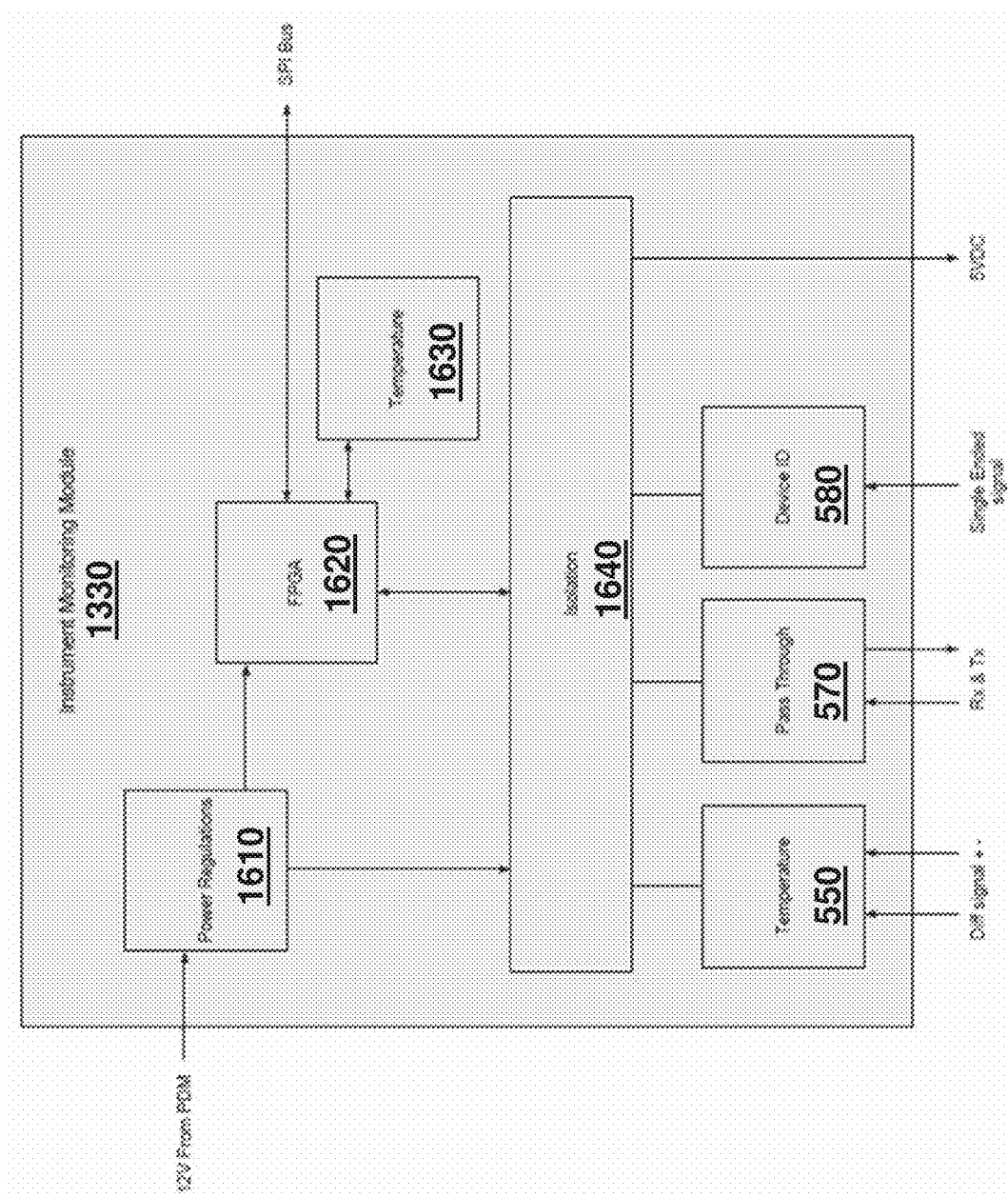
FIG. 16 is a circuit block diagram of an instrument monitoring module of the microwave generator of FIG. 13 according to another embodiment of the present disclosure.

FIG. 16 is a circuit block diagram of an instrument monitoring module 1330 of the microwave generator 1300 of FIG. 13 according to another embodiment of the present disclosure. The instrument monitoring module 1330 includes FPGA 1620 for monitoring the temperature provided by the temperature sensor 1630 disposed in the instrument monitoring module 1330, the power generated by the power regulation circuit or block 1610, and transmits and/or receives data from instrument temperature monitor 550 that connects to a temperature sensor disposed on or near the microwave instrument (not shown), a pass through circuit 570, or device ID reader 580. The power regulation block 1610 receives and monitors the DC voltage provided from the power distribution module 1315, and conditions the DC voltage for the electronics of the instrument monitoring module 1330. In embodiments, the instrument monitoring module 1330 monitors the health of the microwave instrument.

The power regulation circuit or block 1610 supplies DC voltage, e.g., 5 VDC, to the microwave instrument via the isolation device 1640. The isolation device 1640 may be a transformer or other similar circuitry for electrically isolating the microwave instrument (not shown) from the instrument monitoring module 1330.

Figure 17:
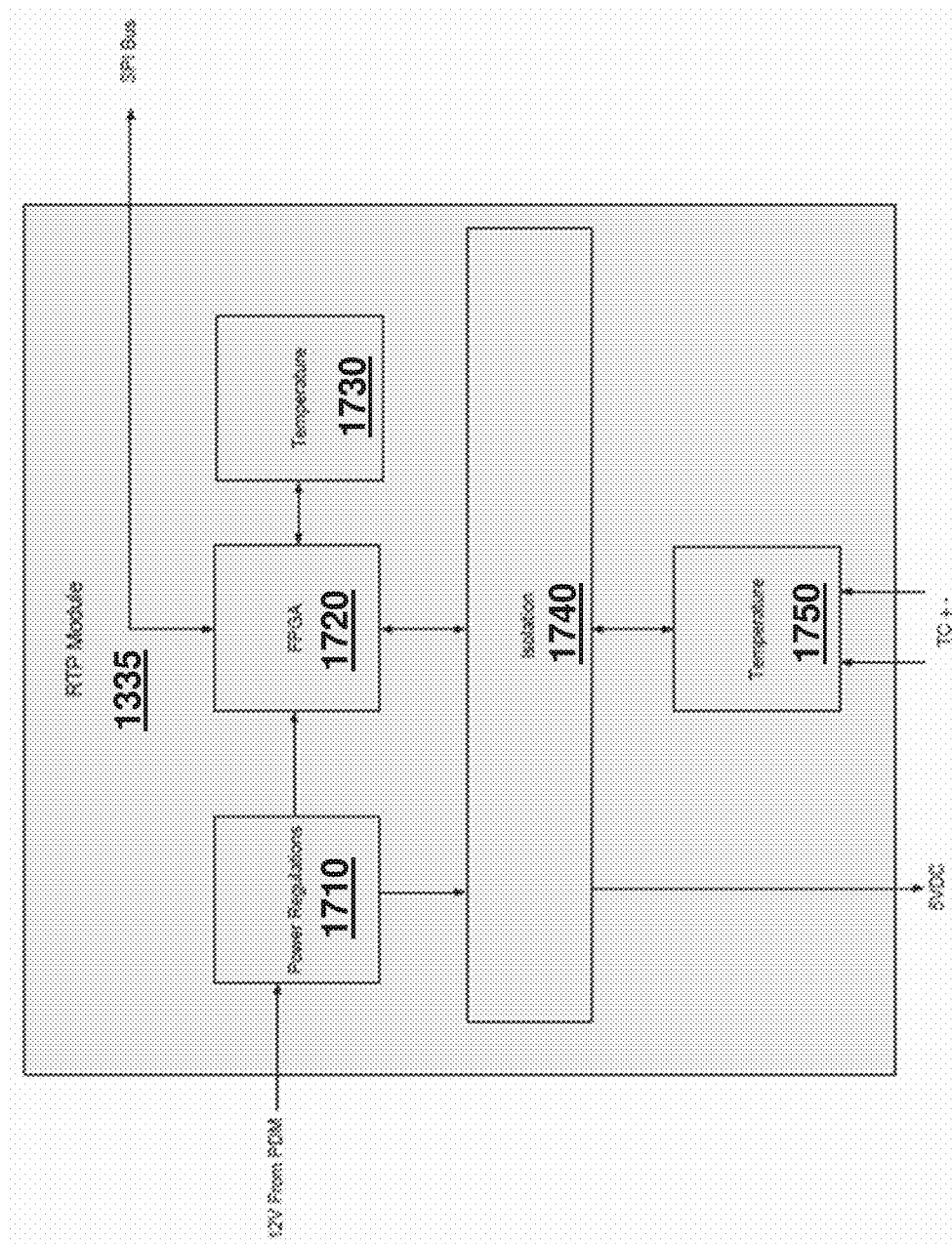
FIG. 17 is a circuit block diagram of a remote temperature probe module of the microwave generator of FIG. 13 according to another embodiment of the present disclosure.

FIG. 17 is a circuit block diagram of a remote temperature probe (RTP) monitoring module 1335 of the microwave generator 1300 of FIG. 13 according to another embodiment of the present disclosure. The RTP monitoring module 1335 includes FPGA 1720 for monitoring the temperature provided by the temperature sensor 1730 disposed in the RTP module 1335, the power generated by the power regulation circuit or block 1710, and transmits and/or receives data from an RTP port or interface 1750 that connects to an RTP (not shown). The power regulation block 1710 supplies DC voltage, e.g., 5 VDC, to the RTP via the isolation device 1740, which isolates the internal electronics of the RTP module 1335 from the patient-side electronics, e.g., the electronics of the remote temperature probe.

Figure 18:
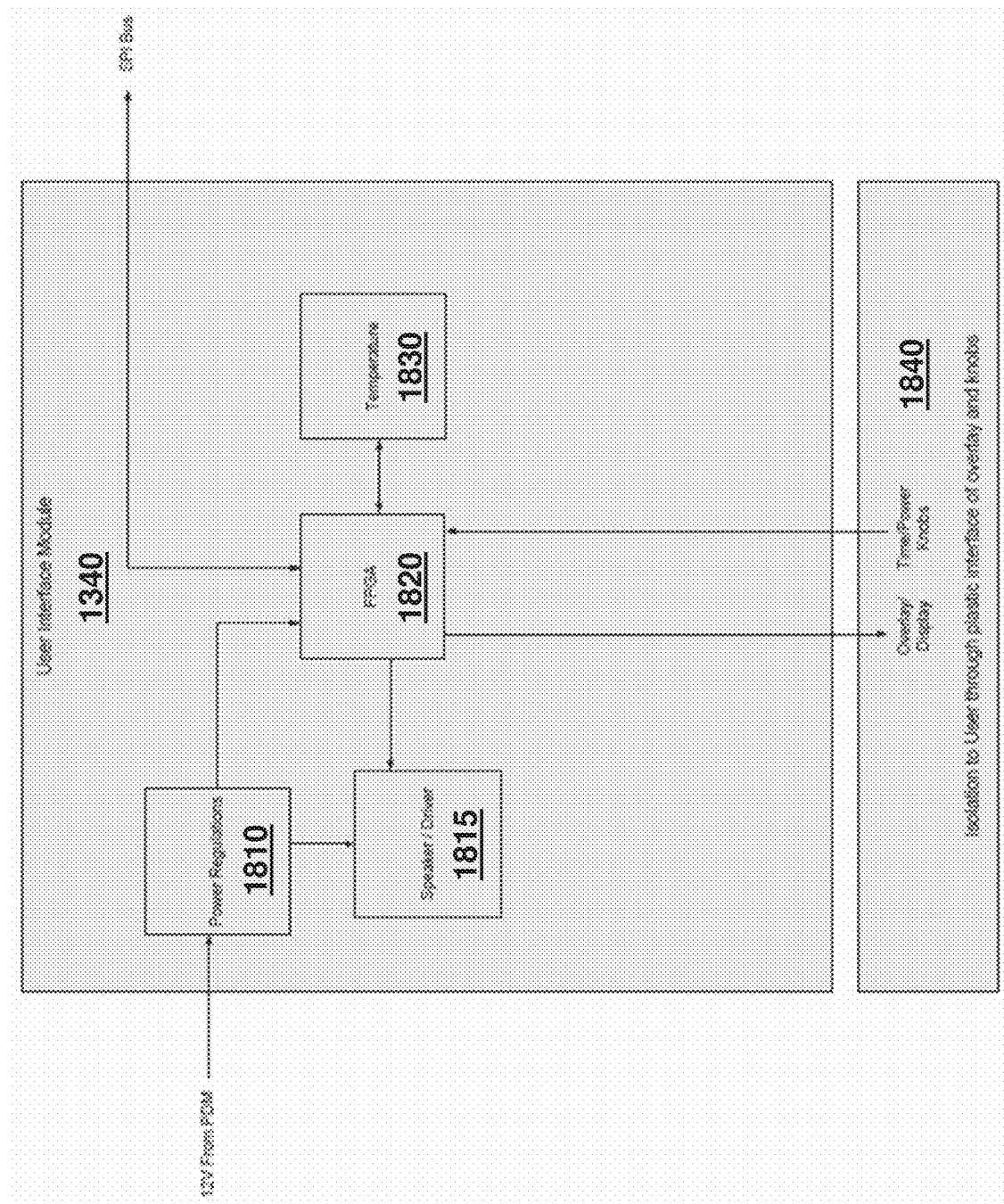
FIG. 18 is a circuit block diagram of a user interface module of the microwave generator of FIG. 13 according to another embodiment of the present disclosure.

FIG. 18 is a circuit block diagram of a user interface module of the microwave generator 1300 of FIG. 13 according to another embodiment of the present disclosure. The RTP module includes FPGA 1820 for monitoring the temperature provided by the temperature sensor 1830 incorporated into the user interface module 1340, the power generated by the power regulation circuit or block 1810, and transmits and/or receives data from a display and time and power knobs. Electrical isolation from the user is provided via the physical plastic of the overlay on the display and the knobs 1840. The FPGA 1820 is configured to provide audio signals to speaker/driver circuitry 1815, which includes a driver which provides drive signals to speakers incorporated into the chassis of the microwave generator 1300.

The power regulation block 1810 monitors the input voltage and regulates it to a voltage level needed to power the electronic components of the user interface module 1340. The power regulation block 1810, which is similar to the power regulation blocks incorporated into the other modules of the microwave generator 1300, allows for inter-module power regulation so that appropriate voltages are supplied to various components of the modules of the microwave generator 1300. For example, the power distribution module 1315 steps down the voltage from higher DC voltages (e.g., 30-40 VDC) to lower DC voltages (e.g., 12V). The power regulation circuits or blocks, e.g., power regulation blocks 1410, 1510, 1610, 1710, and 1810, incorporated into each of the modules then further step down the lower DC voltages (e.g., 12V) to the local power supply requirements (e.g., 5V, 3.3V, etc.). The inter-module power regulation, e.g., via power regulation blocks 1410, 1510, 1610, 1710, and 1810, allows for each of the modules of the microwave generator 1300 to independently meet its power requirements without depending on external power circuitry.

Figure 19:
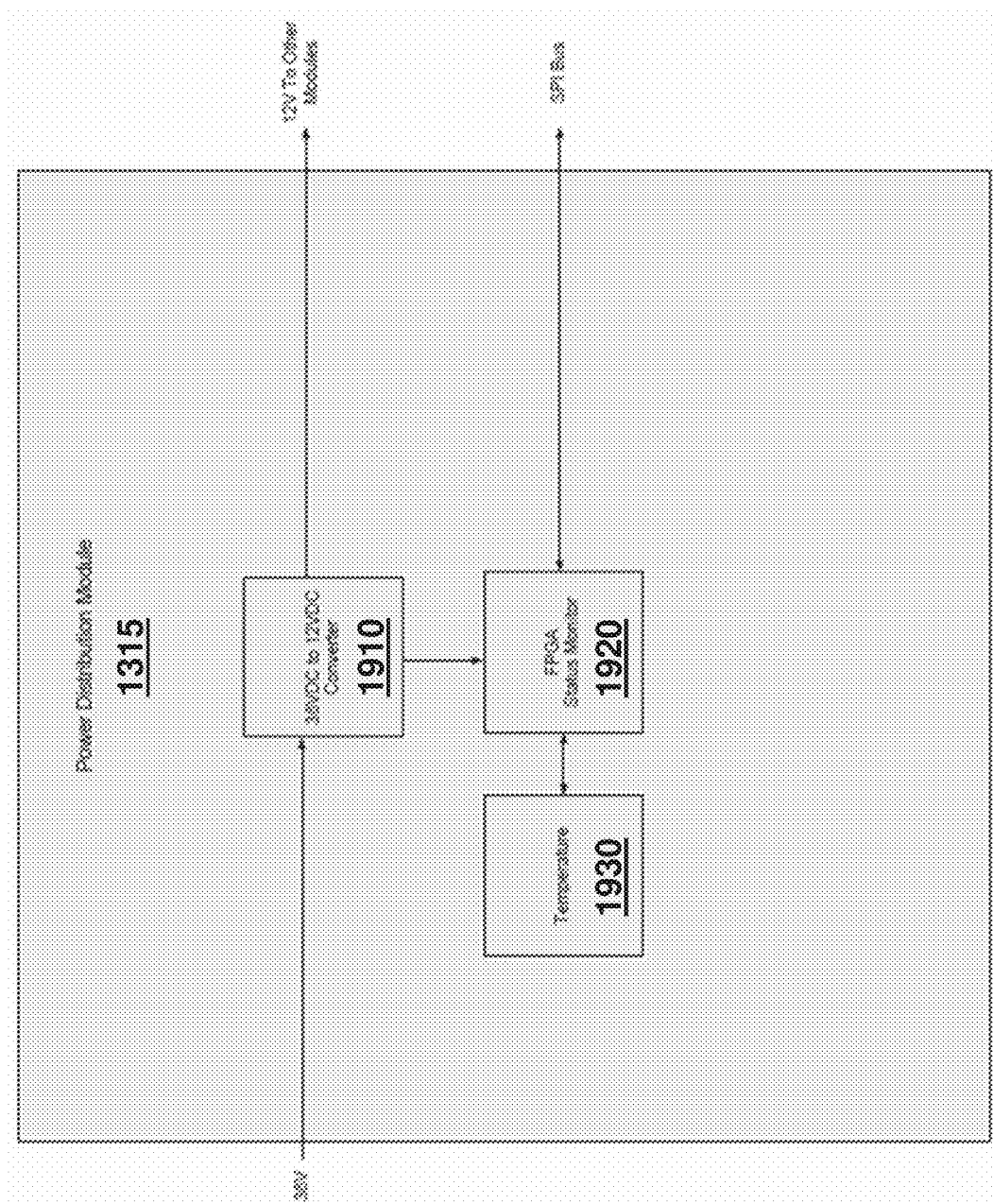
FIG. 19 is a circuit block diagram of a power distribution module of the microwave generator of FIG. 13 according to an embodiment of the present disclosure.

FIG. 19 is a circuit block diagram of a power distribution module 1315 of the microwave generator 1300 of FIG. 13 according to an embodiment of the present disclosure. The power distribution module 1315 includes a DC/DC converter 1910, FPGA 1920, and a temperature sensor 1930. The FPGA 1920 runs firmware that monitors the temperature provided by the temperature sensor 1930 and the DC/DC converter 1910. In embodiments, the DC/DC converter 1910 steps down the voltage, e.g., from 36 VDC to 12 VDC.

Figure 20:
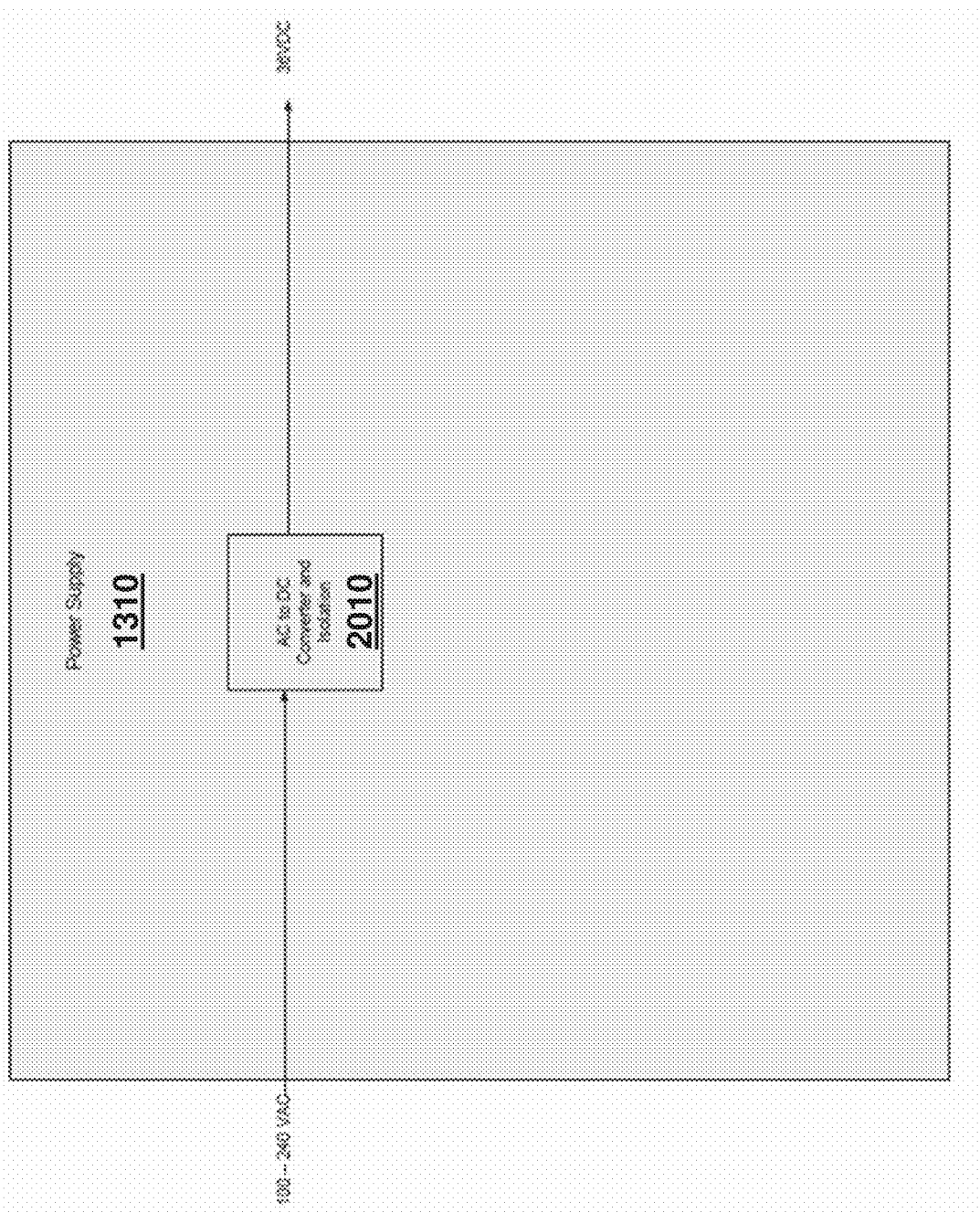
FIG. 20 is a circuit block diagram of a power distribution module of the microwave generator of FIG. 13 according to an embodiment of the present disclosure.

FIG. 20 is a circuit block diagram of the power supply 1310 of the microwave generator 1300 of FIG. 13. The power supply module or power supply 1310 includes AC/DC converter and isolation circuitry 2010. In embodiments, the AC/DC converter and isolation circuitry 2010 converts an AC voltage, e.g., 100-240 VAC, to a DC voltage, e.g., 36 VDC. The AC/DC converter and isolation circuitry 2010 includes isolation circuitry that electrically isolates the electronic components of microwave generator 1300 from the AC input.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A microwave generator, comprising:
   a microwave signal generator configured to generate a microwave signal;
   a generator controller in communication with the microwave signal generator;
   a power supply configured to supply output power to the microwave signal generator and the generator controller;
   a terminal configured to removably couple at least one interchangeable auxiliary module to the microwave generator independent from the microwave signal generator and the generator controller, the at least one interchangeable auxiliary module configured to perform, independently of the microwave signal generator, at least one auxiliary operation of the microwave generator;
   a power distribution module electrically coupled to the power supply and configured to step down the output power supplied by the power supply for providing a stepped-down power output to the generator controller; and
   a power regulation circuit configured to:
      receive the stepped-down power output provided by the power distribution module; and
      further step down the stepped-down power output provided by the power distribution module for providing a level of power to the generator controller that is specific to a power requirement of the generator controller.

2. The microwave generator according to claim 1, wherein the at least one interchangeable auxiliary module is configured to perform, in addition to the at least one auxiliary operation of the microwave generator, an operation of the microwave generator provided to the at least one interchangeable auxiliary module by the microwave signal generator.

3. The microwave generator according to claim 1, wherein the at least one interchangeable auxiliary module is an instrument monitoring module configured to receive information relating to a state or identity of an instrument coupled to the microwave generator.

4. The microwave generator according to claim 1, wherein the at least one interchangeable auxiliary module is configured to receive a signal from a temperature sensor disposed within a microwave ablation instrument coupled to the microwave generator for monitoring the temperature of the microwave ablation instrument.

5. The microwave generator according to claim 1, wherein the at least one interchangeable auxiliary module includes an auxiliary controller that controls the at least one interchangeable auxiliary module independent from the generator controller.

6. The microwave generator according to claim 5, wherein the at least one interchangeable auxiliary module includes a digital bus isolator that transmits data from the auxiliary controller to the generator controller while electrically isolating the at least one interchangeable auxiliary module.

7. The microwave generator according to claim 5, wherein the at least one interchangeable auxiliary module includes a power isolation transformer that transfers power from the power supply to the auxiliary controller while electrically isolating the at least one interchangeable auxiliary module, the auxiliary controller configured to transmit data to the generator controller such that the generator controller controls the microwave signal generator based on the transmitted data.

8. The microwave generator according to claim 1, wherein the at least one interchangeable auxiliary module is configured to draw power from the power supply upon coupling of the at least one interchangeable auxiliary module to the terminal, wherein the draw of power is configured to be detected by the generator controller to provide an indication to the generator controller that the at least one interchangeable auxiliary module is coupled to the terminal.

9. The microwave generator according to claim 1, wherein the generator controller is configured to communicate a query signal to the terminal for determining if the at least one interchangeable auxiliary module is coupled to the terminal.

10. The microwave generator according to claim 9, wherein the terminal is configured to provide power from the power supply to the at least one interchangeable auxiliary module based on a response from the terminal to the query signal communicated from the generator controller.

11. The microwave generator according to claim 1, wherein the power regulation circuit is disposed within the generator controller.

12. A microwave generator, comprising:
   a microwave signal generator configured to generate a microwave signal;
   a generator controller in communication with the microwave signal generator;
   a power supply configured to supply output power to the microwave signal generator and the generator controller;
   a power distribution module electrically coupled to the power supply and configured to step down the output power supplied by the power supply for providing a stepped-down power output to the generator controller; and
   a power regulation circuit disposed within the generator controller and configured to:
      receive the stepped-down power output provided by the power distribution module; and
      further step down the stepped-down power output provided by the power distribution module for providing a level of power to the generator controller that is specific to a power requirement of the generator controller.

13. The microwave generator according to claim 11, further comprising a user interface module configured to operably couple to a user interface of the microwave generator and communicate user input received at the user interface to the generator controller for controlling the microwave signal generator.

14. The microwave generator according to claim 11, further comprising a terminal configured to removably couple at least one interchangeable auxiliary module to the microwave generator independent from the microwave signal generator and the generator controller, the at least one interchangeable auxiliary module configured to perform, independently of the microwave signal generator, at least one auxiliary operation of the microwave generator.

15. The microwave generator according to claim 14, wherein the at least one interchangeable auxiliary module is configured to perform, in addition to the at least one auxiliary operation of the microwave generator, an operation of the microwave generator provided to the at least one interchangeable auxiliary module by the microwave signal generator.

16. The microwave generator according to claim 14, wherein the at least one interchangeable auxiliary module is an instrument monitoring module configured to receive information relating to a state or identity of an instrument coupled to the microwave generator.

17. The microwave generator according to claim 14, wherein the at least one interchangeable auxiliary module is configured to receive a signal from a temperature sensor disposed within a microwave ablation instrument coupled to the microwave generator for monitoring the temperature of the microwave ablation instrument.

18. The microwave generator according to claim 14, wherein the at least one interchangeable auxiliary module includes an auxiliary controller that controls the at least one interchangeable auxiliary module independent from the generator controller.

19. The microwave generator according to claim 18, wherein the at least one interchangeable auxiliary module includes a digital bus isolator that transmits data from the auxiliary controller to the generator controller while electrically isolating the at least one interchangeable auxiliary module.

20. A microwave generator, comprising:
   a microwave signal generator configured to generate a microwave signal;
   a generator controller in communication with the microwave signal generator;
   a power supply configured to supply output power to the microwave signal generator and the generator controller;
   a power distribution module electrically coupled to the power supply and configured to step down the output power supplied by the power supply for providing a stepped-down power output to the generator controller; and
   a power regulation circuit disposed within the generator controller and configured to further step down the stepped-down power output provided by the power distribution module for providing a level of power to the generator controller that is specific to a power requirement of the generator controller.

* * * * *